(12) United States Patent
Liu et al.

(10) Patent No.: US 11,542,308 B2
(45) Date of Patent: Jan. 3, 2023

(54) FLT3 LIGAND FUSION PROTEINS AND METHODS OF USE

(71) Applicant: Genentech, Inc., South San Francisco, CA (US)

(72) Inventors: Yichin Liu, Burlingame, CA (US); Christine Carine Moussion, Redwood City, CA (US); Travis William Bainbridge, Woodside, CA (US); Iraj Hosseini, San Carlos, CA (US); Gregory Alan Lazar, Pacifica, CA (US); Sivan Cohen, San Mateo, CA (US); Christopher Charles Kemball, El Cerrito, CA (US); Jill M. Schartner, Brisbane, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/664,589

(22) Filed: May 23, 2022

(65) Prior Publication Data
US 2022/0289803 A1 Sep. 15, 2022

Related U.S. Application Data

(63) Continuation of application No. PCT/US2021/044586, filed on Aug. 5, 2021.

(60) Provisional application No. 63/062,713, filed on Aug. 7, 2020.

(51) Int. Cl.
| | |
|---|---|
| *C07K 14/475* | (2006.01) |
| *A61K 38/18* | (2006.01) |
| *A61K 31/713* | (2006.01) |
| *A61K 39/395* | (2006.01) |
| *C07K 16/28* | (2006.01) |
| *A61K 39/00* | (2006.01) |

(52) U.S. Cl.
CPC .......... *C07K 14/475* (2013.01); *A61K 31/713* (2013.01); *A61K 38/18* (2013.01); *A61K 39/39541* (2013.01); *C07K 16/2818* (2013.01); *C07K 16/2827* (2013.01); *A61K 2039/505* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,368,114 B2 | 5/2008 | Arthos et al. | |
| 8,871,204 B2* | 10/2014 | Brezski | C07K 16/2863 530/387.3 |
| 9,486,519 B2 | 11/2016 | Sahin et al. | |
| 9,815,880 B2 | 11/2017 | Scheer et al. | |
| 11,124,582 B2* | 9/2021 | Ambrogelly | C07K 14/52 |
| 2004/0022760 A1* | 2/2004 | McKenna | A61K 39/001156 424/85.1 |
| 2005/0232931 A1 | 10/2005 | Ma et al. | |
| 2009/0215991 A1 | 8/2009 | Lazar et al. | |
| 2009/0311247 A1 | 12/2009 | Priest et al. | |
| 2011/0053863 A1 | 3/2011 | Lyman et al. | |
| 2019/0209649 A1 | 7/2019 | Wu et al. | |
| 2019/0216897 A1* | 7/2019 | Klechevsky | A61K 38/217 |
| 2020/0069733 A1* | 3/2020 | Schreiber | C07K 14/7056 |
| 2021/0070887 A1* | 3/2021 | Ambrogelly | A61P 31/18 |
| 2022/0177550 A1* | 6/2022 | Kley | A61P 37/04 |

FOREIGN PATENT DOCUMENTS

| | | |
|---|---|---|
| WO | 2012/146934 | 11/2012 |
| WO | 2018/071919 | 4/2018 |
| WO | 2019/178101 | 9/2019 |
| WO | 2020/069382 | 4/2020 |
| WO | 202/263830 | 12/2020 |

OTHER PUBLICATIONS

Anandasabapathy et al. Efficacy and safety of CDX-301, recombinant human Flt3L, at expanding dendritic cells and hematopoietic stem cells in healthy human volunteers. Bone Marrow Transplant. 2015; 50(7): 924-930.*
Fry et al. Flt3 ligand enhances thymic-dependent and thymic-independent immune reconstitution. Blood 2004; 104: 2794-2800.*
Hammerich et al. (2019) Systemic clinical tumor regressions and potentiation of PD1 blockade with in situ vaccination. Nature Medicine 25: 814-824.*
Jacobsen et al. Engineering an IgG Scaffold Lacking Effector Function with Optimized Developability. J Biol Chem. 2017; 292(5): 1865-1875.*
Kuhne et al. (2021) Pharmacokinetics and pharmacodynamics of GS-3583 in cynomolgus monkeys. Journal for Immunotherapy of Cancer; vol. 9, Iss. Suppl 2: 847-847.*
Liao et al. (2014) Glucocorticoid-induced TNF receptor family-related protein ligand is requisite for optimal functioning of regulatory CD4+ T cells. Front Immunol. 5: 35; p. 1-7.*
Meng et al. (2012) Immunization with HBsAg—Fc fusion protein induces a predominant production of Th1 cytokines and reduces HBsAg level in transgenic mice. Chin Med J; 125(18): 3266-3272.*
NCBI Accession P49771, Aug. 3, 2022, 5 pages.*
NCT04747470, Jul. 26, 2022, 6 pages.*
Onai et al. Activation of the Flt3 signal transduction cascade rescues and enhances type I interferon-producing and dendritic cell development. J. Exp. Med., (2006) 203: 227-238.*
Rajakumaraswamy et al. (2021) GS-3583, a novel FLT3 agonist Fc fusion protein, to expand conventional dendritic cells in healthy volunteers. Journal of Clinical Oncology 39, No. 15-suppl: 2559-2559.*
Tolcher et al. (2022) Phase 1b study of GS-3583, a novel FLT3 agonist Fc fusion protein, in patients with advanced solid tumors. Journal of Clinical Oncology 40, No. 16-suppl: 2566-2566.*
Tu et al. Robust expansion of dendritic cells in vivo by hydrodynamic FLT3L-FC gene transfer. Journal of Immunological Methods (2014) 413:69-73.*

(Continued)

*Primary Examiner* — Ilia I Ouspenski
(74) *Attorney, Agent, or Firm* — Genentech, Inc.

(57) ABSTRACT

The invention provides an effectorless immunoglobulin Fc protein, fusions of the effectorless Fc protein to a Flt3 ligand, and methods of using the same.

26 Claims, 14 Drawing Sheets

Specification includes a Sequence Listing.

(56) References Cited

OTHER PUBLICATIONS

Tullett et al. (2016) Targeting CLEC9A delivers antigen to human CD141+ DC for CD4+ and CD8+ T cell recognition. JCI Insight. 1(7):e87102; p. 1-12.*

Gerlini et al., "Metastatic Melanoma Secreted IL-10 Down-Regulates CD1 Molecules on Dendritic Cells in Metastatic Tumor Lesions" American Journal of Pathology 165(6):1853-1863 ( 2004).

Hammerich et al., "In Situ Vaccination Improves Efficacy of PD-1 Blockade in Unresponsive Lymphoma Tumors through Induction of a Highly Efficient Cross-Presenting Dendritic Cell Subset Expressing TLR3" Blood ((5 pages)), 130( SUPPL 1):4601 ( 2017).

Jochems et al., "Tumor-infiltrating immune cells and prognosis: the potential link between conventional cancer therapy and immunity" Exp Biol Med 236(5):567579 ( 2011).

Lo, M., et al., "Effector-attenuating Substitutions That Maintain Antibody Stability and Reduce Toxicity in Mice" J Biol Chem 292(9):3900-3908 (Mar. 3, 2017).

Lyman et al., "Cloning of the Human Homologue of the Murine flt3 Ligand: A Growth Factor for Early Hematopoietic Progenitor Cells" Blood 83(10):2795-2801 ( 1994).

Mlecnik et al., "Tumor immunosurveillance in human cancers" Cancer Metastasis Rev 30:5-12 ( 2011).

Savvides et al., "Flt3 ligand structure and unexpected commonalities of helical bundles and cystine knots" nature structural biology 7(6):486-491 ( 2000).

Wang et al., "IgG Fc engineering to modulate antibody effector functions" Protein & Cell 9(1):63-73 ( 2017).

Armour, K et al., "Recombinant human IgG molecules lacking Fcÿ receptor I binding and monocyte triggering activities" Eur J Immunol 29(8):2613-2624 (Aug. 1, 1999).

Database Geneseq [Online] Jun. 14, 2018 (Jun. 14, 2018), "Human IL 15R alpha-Fc-1gG1 mutant protein C220S/S267K SEQ:651.", retrieved from EBI accession No. GSP:BFF55911 Database accession No. BFF55911.

* cited by examiner

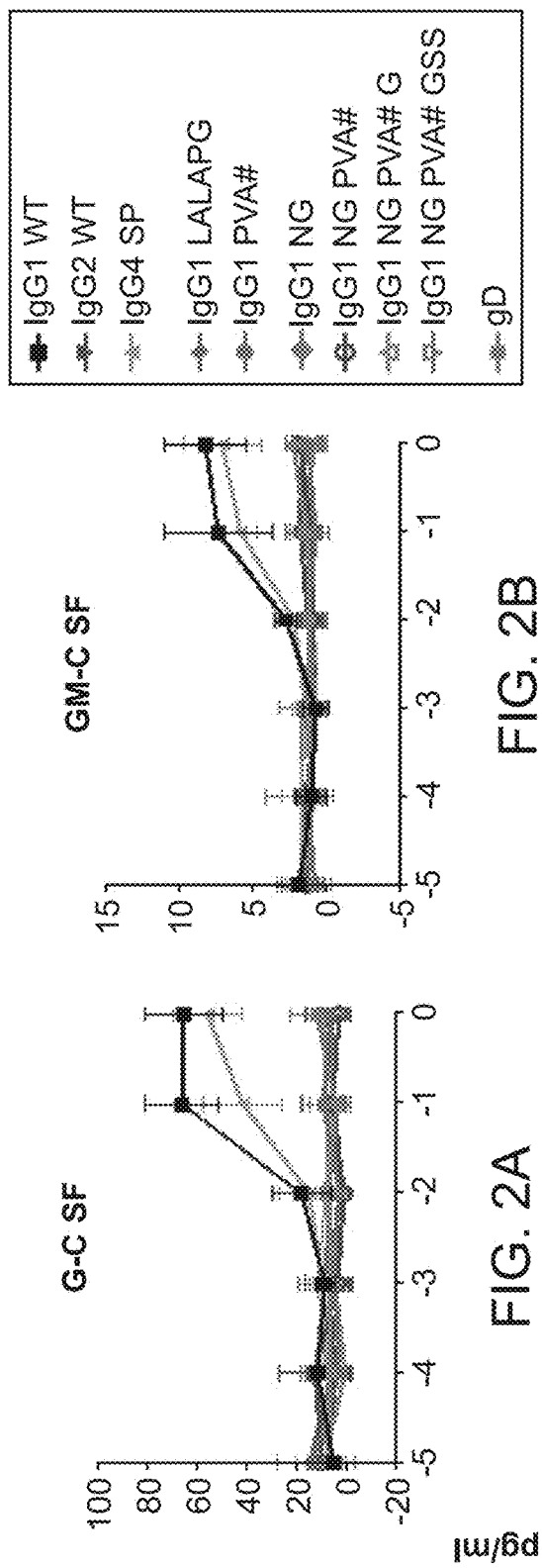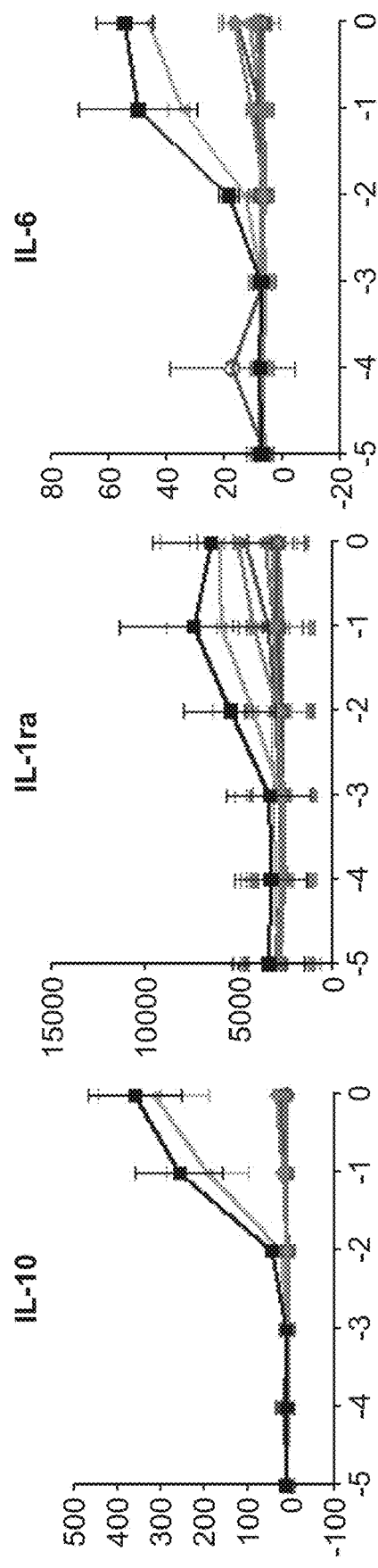
FIG. 2A, FIG. 2B, FIG. 2C, FIG. 2D, FIG. 2E

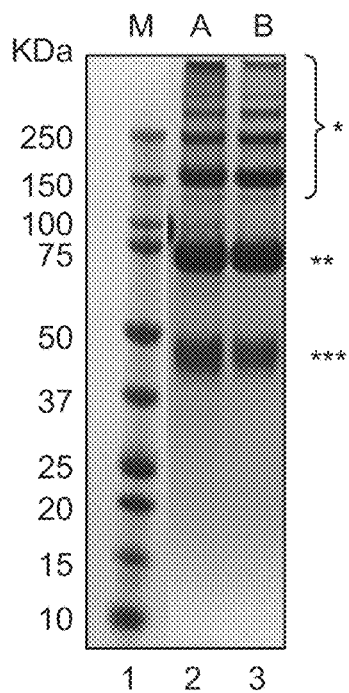
A    Produced in CHO cells
B    Produced in 293 cells
M    MW Marker
\*    Aggregate
\*\*    Dimer
\*\*\*    Monomer
FIG. 3A
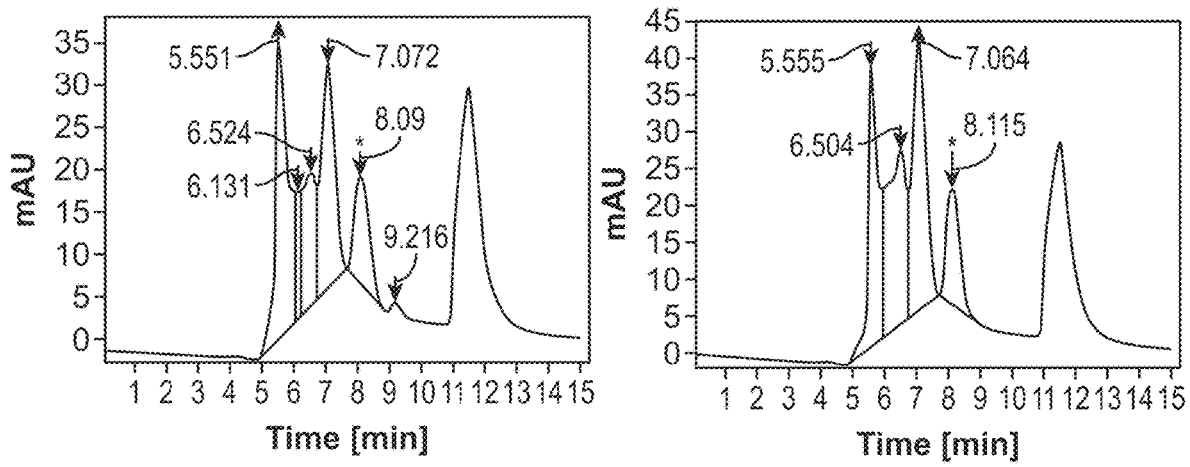
FIG. 3B
| | RetTime (min) | Area (mAU*s) | Area% |
|---|---|---|---|
| * { | 5.551 | 937.6306 | 33.6246 |
| | 6.131 | 150.3570 | 5.3920 |
| | 6.524 | 449.2500 | 16.1107 |
| | 7.072 | 818.1812 | 29.3410 |
| ** | 8.090 | 409.0984 | 14.6708 |
| | 9.216 | 24.0047 | 0.8608 |
FIG. 3C
| | RetTime (min) | Area (mAU*s) | Area% |
|---|---|---|---|
| * { | 5.555 | 856.8539 | 25.1393 |
| | 6.504 | 1007.4920 | 29.5589 |
| | 7.064 | 1105.0417 | 32.4209 |
| ** | 8.115 | 439.0325 | 12.8808 |

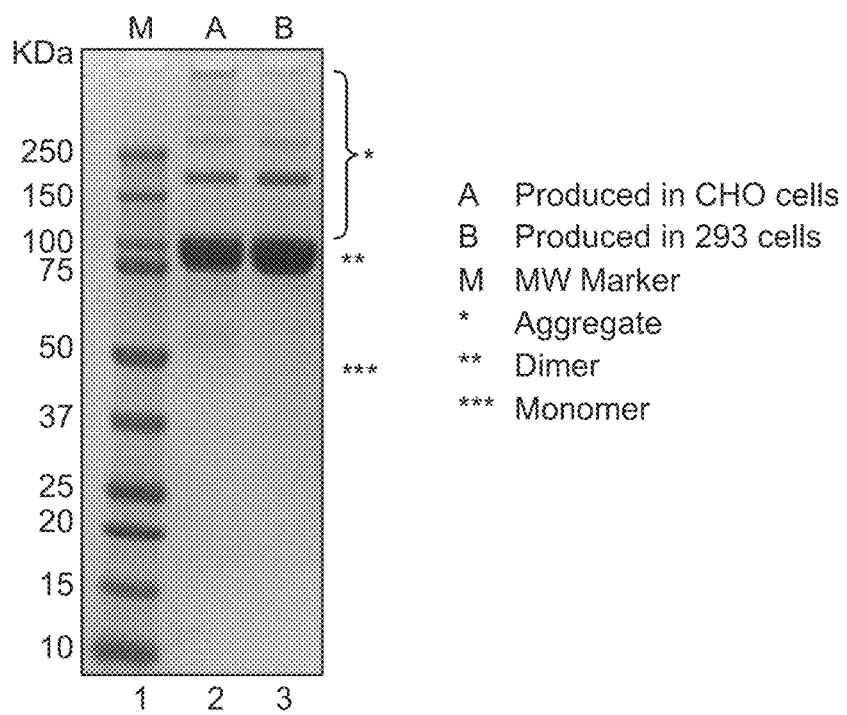
FIG. 3D
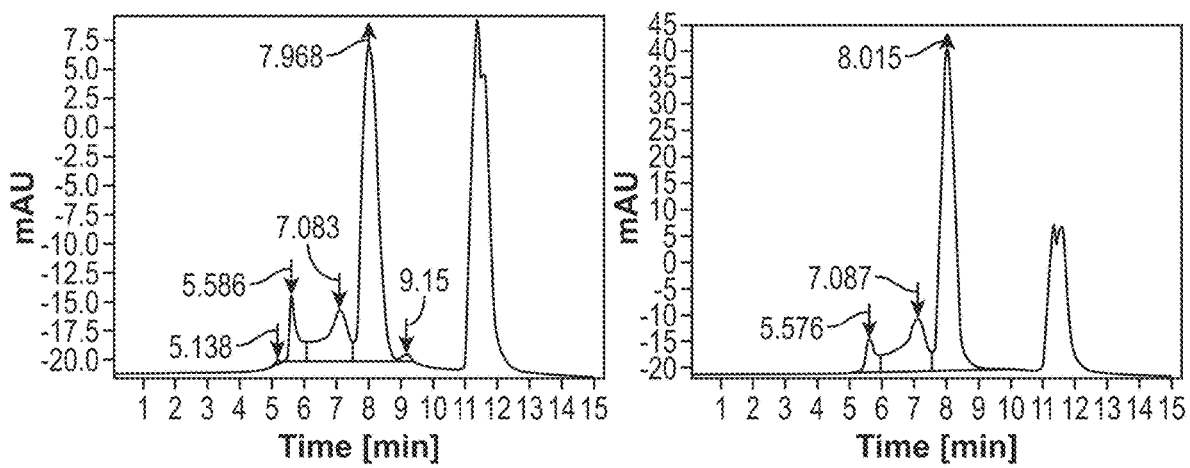
FIG. 3E
FIG. 3F

FLT3 LIGAND FUSION PROTEINS AND METHODS OF USE

CROSS REFERENCE TO RELATED APPLICATIONS

This application is a continuation of International Application No. PCT/US2021/044586 filed on Aug. 5, 2021, which claims priority to and the benefit of U.S. provisional patent application Ser. No. 63/062,713, filed on Aug. 7, 2020, the contents of which are incorporated herein by reference in their entirety.

SEQUENCE LISTING

This application contains a Sequence Listing which has been submitted electronically in ASCII format and is hereby incorporated by reference in its entirety. Said ASCII copy, created on May 19, 2022, is named P36298-US-1_sequence_listing.txt and is 128,444 bytes in size.

FIELD OF THE INVENTION

The present invention relates to Flt3 ligand fusion proteins and methods of using the same.

BACKGROUND

Numerous studies support the importance of the differential presence of immune system components in cancer progression (Jochems and Schlom, Exp Biol Med, 236(5): 567-579 (2011)). Clinical data suggest that high densities of tumor-infiltrating lymphocytes are linked to improved clinical outcome (Mlecnik et al., Cancer Metastasis Rev.; 30: 5-12, (2011)). Tumor immune infiltrates include macrophages, dendritic cells (DC), mast cells, natural killer (NK) cells, nave and memory lymphocytes, B cells and effector T cells (T lymphocytes), primarily responsible for the recognition of antigens expressed by tumor cells and subsequent destruction of the tumor cells by T cells.

Despite presentation of antigens by cancer cells and the presence of immune cells that could potentially react against tumor cells, in many cases the immune system does not get activated or is affirmatively suppressed. Tumors develop a number of immunomodulatory mechanisms to evade anti-tumor immune responses. The overall result is impaired T-cell responses and induction of apoptosis or reduced anti-tumor immune capacity of $CD8^+$ cytotoxic T cells. Inhibition of antigen-presenting functions and dendritic cell (DC) additionally contributes to the evasion of anti-tumor immunity (Gerlini et al. Am. J. Pathol. 165(6), 1853-1863 (2004).

Additionally, the local immunosuppressive nature of the tumor microenvironment can lead to the escape of cancer cell subpopulations that do not express the target antigens. Thus, finding an approach that would promote the preservation and/or restoration of anti-tumor activities of the immune system would be of considerable therapeutic benefit.

Immune checkpoints have been implicated in the tumor-mediated downregulation of anti-tumor immunity. It has been demonstrated that T cell dysfunction occurs concurrently with an induced expression of the inhibitory receptors, CTLA-4 and programmed death 1 polypeptide (PD-1), members of the CD28 family receptors. Nevertheless, despite extensive research in recent years, the success of immunotherapy in a clinical setting has been limited. Few therapeutic agents have been approved by regulatory authorities, and among those, the benefit is not experienced by a majority of patients. In recent years, immune checkpoints have been implicated in the downregulation of anti-tumor immunity and used as therapeutic targets. These observations highlight the need for development of novel therapeutic approaches for harnessing the immune system against cancer.

Human Flt3L (Fms-like tyrosine kinase 3 ligand), a type I transmembrane protein that stimulates the proliferation of bone marrow cells, was cloned for in 1994 (Lyman et al., 1994). The use of soluble hFlt3L has been explored in various preclinical and clinical settings including stem cell mobilization in preparation for bone marrow transplantation, cancer immunotherapy such as expansion of dendritic cells, as well as an vaccine adjuvant. Yet no pharmaceutical composition based on Flt3L has progressed past Phase 2 in the clinic.

One challenge is to optimize exposure to the Flt3L ligand and identify an optimal dosing regimen while minimizing adverse side effects or potential unfavorable immunologic effects. Modulating exposure can be done, for example, by varying dosing regimens, varying dosing amounts, or changing the pharmacokinetic and/or pharmacodynamics properties of the therapeutic molecule. Provided herein is a Flt3L-Fc fusion protein having beneficial PK/PD properties beneficial for enhancing immunotherapy for cancer patients.

SUMMARY

The invention provides an effectorless Fc protein, fusion proteins comprising the effectorless Fc protein, including Flt3 ligand fusion proteins comprising an active Flt3 ligand (Flt3L) fused to the effectorless immunoglobulin Fc protein and methods of using the same. Methods for use of the effectorless Fc protein, fusion proteins comprising the effectorless Fc protein, and Flt3L-Fc fusion proteins include treatment of cancer, especially treatment of cancer in patients receiving checkpoint immunotherapy. The invention further provides an effectorless IgG Fc protein.

In one aspect, an effectorless Fc protein is provided, comprising an amino acid sequence which is at least 95%, 96%, 97%, 98%, or 99% identical to residues SEQ ID NO:13, wherein residues 13-17 of SEQ ID NO:13 comprise the amino acid sequence PVAGP (SEQ ID NO:20) or residue 76 of SEQ ID NO:13 is a glycine. In other embodiments, the effectorless IgG1 Fc region comprises an amino acid sequence which is at least 95%, 96%, 97%, 98%, or 99% identical to SEQ ID NO:13, wherein residues 13-17 of SEQ ID NO:13 comprise the amino acid sequence PVAGP (SEQ ID NO:20) and residue 76 of SEQ ID NO:13 is a glycine. In still other embodiments, the effectorless IgG1 Fc region comprises an amino acid sequence which is identical to SEQ ID NO:13. For clarity, in some embodiments, wherein residues 13-17 of SEQ ID NO:13 comprise PVAGP (SEQ ID NO:20), this may be referred to herein as encompassing the PVA# variant, and wherein residue 76 of SEQ ID NO:13 is a glycine, this may be referred to herein as the N297G mutations, wherein 297 refers to EU numbering of antibodies.

In some embodiments, an effectorless Fc protein comprises the protein sequence of SEQ ID NO: 2, 4, 5, 6, 13, or 15.

In still other embodiments, the effectorless IgG1 Fc protein is attenuated relative to a wildtype IgG1 Fc region which comprises SEQ ID NO:12.

In some aspects, an antibody is provided comprising the effectorless Fc protein which comprises an amino acid sequence which is at least 95%, 96%, 97%, 98%, or 99% identical to residues SEQ ID NO:13, wherein residues 13-17 of SEQ ID NO:13 comprise the amino acid sequence PVAGP (SEQ ID NO:20) or residue 76 of SEQ ID NO:13 is a glycine.

In some embodiments, the antibody binds to the Flt3L receptor.

In some embodiments, the antibody binds to a checkpoint inhibitor protein. In other embodiments, the checkpoint inhibitor protein is PD-L1, PD-1, and/or CTLA-4. In some embodiments, the antibody is a bispecific antibody.

In some aspects, a heterodimeric protein is provided comprising the effectorless Fc protein of the present disclosure and a second protein. In some embodiments, the effectorless Fc protein and the second protein are covalently linked to each other. In other embodiments, the effectorless Fc protein and the second protein are linked by a disulfide bond.

In some aspects, an isolated nucleic acid encoding an effectorless Fc protein of the present disclosure, an antibody that comprises the effectorless Fc protein, and/or the heterodimeric protein comprising the effectorless Fc protein as described herein and above is provided. In some embodiments, the isolated nucleic acid encodes the protein sequence of SEQ ID NO: 2, 4, 5, 6, 13, or 15. In other embodiments, the isolated nucleic acid further encodes a signal sequence at the N-terminal end of the effectorless Fc protein. In a preferred example, the isolated nucleic acid encodes the protein sequence of SEQ ID NO:13.

In some aspects, a host cell comprising a nucleic acid encoding the effectorless Fc protein of the present disclosure, a fusion protein comprising the effectorless Fc protein, an antibody that comprises the effectorless Fc protein, and/or the heterodimeric protein comprising the effectorless Fc protein as described herein and above is provided.

In some aspects a method of producing an effectorless Fc protein of the present disclosure, a fusion protein comprising the effectorless Fc protein, an antibody that comprises the effectorless Fc protein, and/or the heterodimeric protein comprising the effectorless Fc protein is provided, comprising culturing the host cell comprising a nucleic acid encoding the effectorless Fc protein of the present disclosure, a fusion protein comprising the effectorless Fc protein, an antibody that comprises the effectorless Fc protein, and/or the heterodimeric protein comprising the effectorless Fc protein so that each of the proteins is produced. In some embodiments, the method further comprises recovering the effectorless Fc protein of the present disclosure, a fusion protein comprising the effectorless Fc protein, an antibody that comprises the effectorless Fc protein, and/or the heterodimeric protein comprising the effectorless Fc protein from the host cell. In some embodiments, the host cell is a eukaryotic cell or a prokaryotic cell. In other embodiments, the eukaryotic cell is a CHO cell.

In some aspects, a host cell comprising a nucleic acid encoding an effectorless Fc protein of the present disclosure, a fusion protein comprising the effectorless Fc protein, an antibody that comprises the effectorless Fc protein, and/or the heterodimeric protein comprising the effectorless Fc protein is provided.

In some aspects a method of producing an effectorless Fc protein of the present disclosure, a fusion protein comprising the effectorless Fc protein, an antibody that comprises the effectorless Fc protein, and/or the heterodimeric protein comprising the effectorless Fc protein is provided, comprising culturing the host cell comprising a nucleic acid encoding the effectorless Fc protein of the present disclosure, a fusion protein comprising the effectorless Fc protein, an antibody that comprises the effectorless Fc protein, and/or the heterodimeric protein comprising the effectorless Fc protein so that the effectorless Fc protein of the present disclosure, a fusion protein comprising the effectorless Fc protein, an antibody that comprises the effectorless Fc protein, and/or the heterodimeric protein comprising the effectorless Fc protein is produced. In some embodiments, the method further comprises recovering the effectorless Fc protein of the present disclosure, a fusion protein comprising the effectorless Fc protein, an antibody that comprises the effectorless Fc protein, and/or the heterodimeric protein comprising the effectorless Fc protein from the host cell. In some embodiments, the host cell is a eukaryotic cell or a prokaryotic cell. In other embodiments, the eukaryotic cell is a CHO cell.

In one aspect, a fusion protein comprising the effectorless Fc protein is provided comprising the effectorless Fc protein (SEQ ID NO:13 or variant thereof) and a second protein, wherein the second protein is a ligand to a target protein. In some embodiments, the ligand modulates the target protein upon binding of the ligand to the target protein. In some embodiments, the second protein is a Flt3L. In other embodiments, the target protein is the Flt3L receptor. In preferred embodiments, the second protein is N-terminal to the effectorless Fc protein.

In some embodiments, the fusion protein comprises a Fc protein which is at least about 95%, 96%, 97%, 98%, or 99% identical to SEQ ID NO:13, wherein residues 13-17 of SEQ ID NO:13 comprise the amino acid sequence PVAGP (SEQ ID NO:20) or residue 76 of SEQ ID NO:13 is a glycine. In other embodiments, the effectorless IgG1 Fc region comprises an amino acid sequence which is at least 95%, 96%, 97%, 98%, or 99% identical to SEQ ID NO:13, wherein residues 13-17 of SEQ ID NO:13 comprise the amino acid sequence PVAGP (SEQ ID NO:20) and residue 76 of SEQ ID NO:13 is a glycine. In still other embodiments, the effectorless IgG1 Fc region comprises an amino acid sequence which is identical to SEQ ID NO:13. For clarity, in some embodiments, wherein residues 13-17 of SEQ ID NO:13 comprise PVAGP (SEQ ID NO:20), this may be referred to herein as encompassing the PVA# variant, and wherein residue 76 of SEQ ID NO:13 is a glycine, this may be referred to herein as the N297G mutations, wherein 297 refers to EU numbering of antibodies.

In one aspect, the fusion protein comprises a Flt3 ligand (Flt3L) and an effectorless IgG1 Fc region, wherein the Flt3L-Fc fusion protein has an effector function which is attenuated relative to a wildtype IgG1 Fc region which comprises SEQ ID NO:12.

In some embodiments of the Flt3L-Fc fusion protein, the Flt3L comprises a protein comprising an amino acid sequence which is at least 95%, 96%, 97%, 98%, or 99% identical to residues 27-167 of SEQ ID NO:21. In other embodiments, the Flt3L comprises the amino acid sequence of SEQ ID NO:21, wherein the amino acid sequence has 1, 2, or 3 amino acid substitutions. In other embodiments, the 1, 2, or 3 amino acid substitutions are not present in a region of the Flt3L that binds to an FcRn protein. In other embodiments, the Flt3L protein comprises the sequence of SEQ ID NO:22.

In some embodiments of the Flt3L-Fc fusion protein, the Flt3L comprises a protein comprising amino acids 27-167, 27-168, 27-169, 27-170, 27-171, 27-172, 27-173, 27-174, 27-175, 27-176, 27-177, 27-178, 27-179, 27-180, 27-181, 27-182, 27-183, 27-184, or 27-185 of SEQ ID NO:21. In preferred embodiments of the Flt3L-Fc fusion protein, the Flt3L comprises an amino acid sequence consisting of amino acids 27-167 of SEQ ID NO:21 or amino acids 27-168 of SEQ ID NO:21. In other embodiments, the Flt3L of the Flt3L-Fc fusion protein does not comprise 168-235, 169-235, 170-235, 171-235, 172-235, 173-235, of SEQ ID NO:21. In still other embodiments, the Flt3L of the Flt3L-Fc fusion protein does not comprise the amino acid sequence PWSPRPLEATAPTAPQPP (SEQ ID NO:48), WSPR-PLEATAPTAPQPP (SEQ ID NO:49), SPR-PLEATAPTAPQPP (SEQ ID NO:50), PRPLEATAPTAPQPP (SEQ ID NO:51), RPLEATAPTAPQPP (SEQ ID NO:52), or PLEATAPTAPQPP (SEQ ID NO:53).

In some embodiments of the Flt3L-Fc fusion protein, the Flt3L comprises a protein which is at least about 95%, 96%, 97%, 98%, or 99% identical to a protein comprising amino acids 27-167, 27-168, 27-169, 27-170, 27-171, 27-172, 27-173, 27-174, 27-175, 27-176, 27-177, 27-178, 27-179, 27-180, 27-181, 27-182, 27-183, 27-184, or 27-185 of SEQ ID NO:21.

In some embodiments of the Flt3L-Fc fusion protein, the Flt3L comprises a protein which is at least about 95%, 96%, 97%, 98%, 99%, or 100% identical to a protein comprising amino acids 24-167, 25-167, 26-167, 24-168, 25-168, 26-168, 24-169, 25-169, or 26-169 of SEQ ID NO:21.

In some embodiments of the Flt3L-Fc fusion protein, the effectorless IgG1 Fc region comprises an amino acid sequence which is at least 95%, 96%, 97%, 98%, or 99% identical to SEQ ID NO:13, wherein residues 13-17 of SEQ ID NO:13 comprise the amino acid sequence PVAGP (SEQ ID NO:20) or residue 76 of SEQ ID NO:13 is a glycine. In other embodiments, the effectorless IgG1 Fc region comprises an amino acid sequence which is at least 95%, 96%, 97%, 98%, or 99% identical to SEQ ID NO:13, wherein residues 13-17 of SEQ ID NO:13 comprise the amino acid sequence PVAGP (SEQ ID NO:20) and residue 76 of SEQ ID NO:13 is a glycine. In still other embodiments, the effectorless IgG1 Fc region comprises an amino acid sequence which is identical to SEQ ID NO:13. For clarity, in some embodiments, wherein residues 13-17 of SEQ ID NO:13 comprise PVAGP (SEQ ID NO:20), this may be referred to herein as encompassing the PVA# variant, and wherein residue 76 of SEQ ID NO:13 is a glycine, this may be referred to herein as the N297G mutations, wherein 297 refers to EU numbering of antibodies.

In some embodiments, the Flt3L-Fc fusion protein comprises an amino acid sequence which is at least 95%, 96%, 97%, 98%, or 99% identical to SEQ ID NO:26. In other embodiments, the Flt3L-Fc fusion protein comprises the amino acid sequence of SEQ ID NO:26.

In some embodiments, the Flt3L-Fc fusion protein comprises an amino acid sequence which is at least 95%, 96%, 97%, 98%, or 99% identical to SEQ ID NO:26, wherein residues 154-158 of SEQ ID NO:26 comprise the amino acid sequence PVAGP (SEQ ID NO:20) and residue 217 of SEQ ID NO:26 is a glycine.

In some embodiments, the Flt3L-Fc fusion protein comprises an amino acid sequence which is at least 95%, 96%, 97%, 98%, or 99% identical to SEQ ID NO:25, wherein residues 155-159 of SEQ ID NO:25 comprise the amino acid sequence PVAGP (SEQ ID NO:20) and residue 218 of SEQ ID NO:25 is a glycine.

In some embodiments, the Flt3L-Fc fusion protein comprises an amino acid sequence which is at least 95%, 96%, 97%, 98%, or 99% identical to SEQ ID NO:32, wherein residues 153-157 of SEQ ID NO:32 comprise the amino acid sequence PVAGP (SEQ ID NO:20) and residue 216 of SEQ ID NO:32 is a glycine.

In some embodiments, the Flt3L-Fc fusion protein comprises an amino acid sequence which is at least 95%, 96%, 97%, 98%, or 99% identical to SEQ ID NO:33, wherein residues 152-156 of SEQ ID NO:33 comprise the amino acid sequence PVAGP (SEQ ID NO:20) and residue 215 of SEQ ID NO:33 is a glycine.

In some embodiments, the Flt3L-Fc fusion protein comprises an amino acid sequence which is at least 95%, 96%, 97%, 98%, or 99% identical to SEQ ID NO:34, wherein residues 151-154 of SEQ ID NO:34 comprise the amino acid sequence PVAGP (SEQ ID NO:20) and residue 214 of SEQ ID NO:34 is a glycine.

In some embodiments, the Flt3L-Fc fusion protein comprises an amino acid sequence which is at least 95%, 96%, 97%, 98%, 99%, or 100% identical to a protein selected from the group consisting of SEQ ID NO:27 to SEQ ID NO:31 and SEQ ID NO:35 to SEQ ID NO:44.

In some embodiments, the Flt3L-Fc fusion protein activates antibody-dependent cellular phagocytosis (ADCP) in an in vitro assay at an activity level that is less than about 20%, 25%, 30%, 35%, 40%, 45%, 50%, 55%, 60%, 65%, 70%, 75%, 80%, 85%, 90%, 95%, or 99% of the activity level by a Flt3L-Fc fusion protein comprising wildtype Flt3L fused to wildtype IgG1 Fc (SEQ ID NO:12) in the in vitro assay. In other embodiments, ADCP in vitro assay comprises use of primary macrophages as effector cells and a cell line that expresses the Flt3L receptor as target cells. In still other embodiments, the primary macrophages are monocyte-derived macrophages from healthy human donors. In yet other embodiments, the target cells are human acute lymphoblastic leukemia cells, optionally, SEM cell line cells. In some embodiments, the activity is measured as percent phagocytosis (% ADCP), wherein phagocytosis is determined by measuring uptake of a visual marker from the target cells.

In some embodiments, the Flt3L-Fc fusion protein activates DC expansion in a subject that has been administered the fusion protein. In other embodiments, the DC expansion is measured in the whole blood of the subject. In still other embodiments, the DC expansion is measured by flow cytometry or FACS. In some embodiments, the DC expansion is at least 5-fold, 10-fold, 15-fold, 20-fold, 50-fold, 100-fold, 500-fold, 1000-fold, 2000-fold, 5000-fold, or 10,000-fold greater than the DC expansion resulting from administration of a Flt3L protein which is not fused to a heterologous protein. In other embodiments, the heterologous protein is a wildtype human IgG Fc protein. In yet other embodiments, the wildtype human IgG Fc protein is a wildtype IgG1, IgG2, IgG3 or IgG4 Fc protein. In some embodiments, the Flt3L protein is not fused to a wildtype IgG1 Fc protein or to a human serum albumin protein. In some embodiments, the subject is a rodent, a rabbit, a cynomolgus monkey, or a human. In other embodiments, the rodent is a mouse or a rat.

In some embodiments, the Flt3L-Fc fusion protein has an increased thermostability as compared to the thermostability of a Flt3L-Fc fusion protein having SEQ ID NO:14. In other embodiments, the thermostability is measured using differential scanning fluorimetry. In still other embodiments, the Flt3L-Fc fusion protein has a melting temperature (Tm) which is at least 1.5° C., 2° C., 3° C., 4° C. or 5° C. greater than the Tm of the Flt3L-Fc fusion protein having SEQ ID NO:14.

In some embodiments, the Flt3L-Fc fusion protein contains a single amino acid substitution in the Flt3L domain. In other embodiments, the substitution reduces in vivo immunogenicity but does not reduce functional activity by more than 10%, 20%, or 30%. In other embodiments, the functional activity assay is the expansion of dendritic cells in an animal.

In some aspects, an isolated nucleic acid encoding an Flt3L-Fc fusion protein as described herein and above is provided. In some embodiments, the isolated nucleic acid encodes the protein sequence of SEQ ID NO: 25, 26, 27, 28, 29, 30, 31, 32, 33, 34, 35, 36, 37, 38, 39, 40, 41, 42, 43, or 44. In other embodiments, the isolated nucleic acid further encodes a signal sequence which is at the N-terminal end of the Flt3L-Fc fusion protein. In a preferred example, the isolated nucleic acid encodes the protein sequence of SEQ ID NO:45.

In some aspects, a host cell comprising a nucleic acid encoding a Flt3L-Fc fusion protein as described herein and above is provided.

In some aspects a method of producing a Flt3L-Fc fusion protein is provided, comprising culturing the host cell comprising a nucleic acid encoding the effectorless Flt3L-Fc fusion protein so that the Flt3L-Fc fusion protein is produced. In some embodiments, the method further comprises recovering the Flt3L-Fc fusion protein from the host cell. In some embodiments, the host cell is a eukaryotic cell or a prokaryotic cell. In other embodiments, the eukaryotic cell is a CHO cell.

In some aspects, a pharmaceutical formulation is provided, comprising a Flt3L-Fc fusion protein as described herein and a pharmaceutically acceptable carrier.

In some embodiments, the pharmaceutical formulation further comprises an additional therapeutic agent. In still other embodiments, the additional pharmaceutical agent is an adjuvant, a dendritic cell maturation factor, and/or a checkpoint inhibitor.

In some aspects, a method for expanding the number of dendritic cells (DCs) in a subject administered the Flt3L-Fc fusion protein is provided. In some embodiments, the DCs are cDC1 and/or cDC2 cells. In other embodiments, the method comprises administering to the subject a Flt3L-Fc fusion protein of the present invention.

In some embodiments, the method comprises administering to the subject a dose of about 0.1 mg/kg to 50 mg/kg, 0.1 mg/kg to 40 mg/kg, 0.1 mg/kg to 25 mg/kg, 0.1 mg/kg to 20 mg/kg, 0.1 mg/kg to 15 mg/kg, 0.1 mg/kg to 10 mg/kg, 1 mg/kg to 50 mg/kg, 1 mg/kg to 40 mg/kg, 1 mg/kg to 25 mg/kg, 1 mg/kg to 20 mg/kg, 1 mg/kg to 15 mg/kg, or 1 mg/kg to 10 mg/kg of the Flt3L-Fc fusion protein.

In some embodiments, the method comprises administering to the subject the Flt3L fusion protein about once per day, once per week, twice per week, once every 2 weeks, once every 3 weeks, once per month, or once every other month.

In some embodiments, the method comprises administering to the subject the Flt3L fusion protein by intravenous administration, parenteral administration, intramuscular injection, or subcutaneous injection.

In some aspects, a method for treating a cancer is provided, wherein the method comprises administering to a subject in need thereof a Flt3L-Fc fusion protein as described herein. In some embodiments, the method comprising administering a therapeutically effective amount of the Flt3L-Fc fusion protein and administering a therapeutically effective amount of an immune checkpoint inhibitor. In other embodiments, the immune checkpoint inhibitor suppresses or inhibits the effects of PD-1 or PD-L1. In still other embodiments, the immune checkpoint inhibitor is pembrolizumab, nivolumab, pidilizumab, BMS 936559, atezolizumab, or avelumab. In other embodiments, the checkpoint inhibitor is administered before, simultaneously with, or after administration of the Flt3L-Fc fusion protein.

In some embodiments, the method further comprises administering a dendritic cell (DC) maturation factor. In other embodiments, the DC maturation factor is selected from polyIC, poly-ICLC, a CD40 agonist, radiation therapy, and chemotherapy. In other embodiments, the DC maturation factor is administered to the individual prior to, simultaneously with, and/or subsequent to administering the Flt3L-Fc fusion protein. In particular embodiments, the DC maturation factor is radiation therapy. In some embodiments, the method comprises administering the Flt3L-Fc fusion protein to the subject after the subject has received the DC maturation factor. In other embodiments, the method comprises administering the Flt3L-Fc fusion protein to the subject before the subject has received the DC maturation factor. In still other embodiments, method comprises administering the Flt3L-Fc fusion protein to the subject at about the same time that the subject receives the DC maturation factor.

In some embodiments, the cancer is selected from the group consisting of non small cell lung cancer (NSCLC), small cell lung cancer (SCLC), melanoma, Pancreatic ductal adenocarcinoma, (PDAC), triple negative breast cancer (TNBC), non-Hodgkin lymphoma (NHL), colorectal cancer (CRC), breast cancer, bladder cancer, kidney cancer, or a combination thereof.

In some embodiments, the subject was previously treated with a checkpoint inhibitor. In other embodiments, the subject did not respond to the checkpoint inhibitor therapy, wherein the checkpoint inhibitor therapy was administered over a period of at least or about 3 months, 4 months, 5 months, 6 months, 7 months, 8 months, 9 months, 10 months, 1 year, 1.5 years, or 2.

In some embodiments, the subject was treated with radiation therapy, wherein the radiation therapy was administered over a period of at least or about 3 months, 4 months, 5 months, 6 months, 7 months, 8 months, 9 months, 10 months, 1 year, 1.5 years, or 2 years.

In some embodiments, the subject was treated with chemotherapy, wherein the chemotherapy was administered over a period of at least or about 3 months, 4 months, 5 months, 6 months, 7 months, 8 months, 9 months, 10 months, 1 year, 1.5 years, or 2 years.

In some embodiments, the cancer in the subject has been characterized as comprising an immune desert tumor. In other embodiments, the cancer has been characterized as comprising a tumor with reduced inflammation ("cold tumor") relative to a responsive, inflamed tumor ("hot tumor").

BRIEF DESCRIPTION OF THE FIGURES

FIGS. 2A-2E show cytokine release by macrophages when the anti-Her2 antibodies with a wildtype or variant Fc domain are incubated with primary M1 macrophages and SkBr3 target cells. The x-axis shows antibody concentration and the y-axis shows pg/ml cytokine. FIG. 2A: G-CSF; FIG. 2B: GM-CSF; FIG. 2C: IL-10; FIG. 2D: IL-1ra; FIG. 2E: IL-6.

FIG. 2F: IL-8; FIG. 2G: MIP-1 alpha; FIG. 2H: MIP-1 beta; FIG. 2I: RANTES; FIG. 2J: TNFalpha.

FIGS. 3A-3C show differential characteristics of Flt3L-FcNG2LH fusion proteins with respect to aggregation and disulfide bond properties. Analysis of hFLT3L.S163.no.hinge.hIgG1.NG.PVA# aggregation and dimer formation of protein expressed in CHO cells and HEK293 cells is shown by SDS-PAGE (FIG. 3A) and SEC-HPLC (FIG. 3B: 293 cells and (FIG. 3C: HEK297 cells). For FIGS. 3B-3C, the x-axis is time and the y-axis is mAU.

FIGS. 3D-3F show differential characteristics of Flt3L-FcNG2LH fusion proteins with respect to aggregation and disulfide bond properties. Analysis of hFLT3L.P167.5aa.hinge.hIgG1.NG.PVA# aggregation and dimer formation of protein expressed in CHO cells and HEK293 cells is shown by SDS-PAGE (FIG. 3D) and SEC-HPLC (FIG. 3E: 293 cells and FIG. 3F: HEK297 cells). For FIGS. 3E-3F, the x-axis is time and the y-axis is mAU.

FIG. 4A shows a dose response curve of hFLT3L.P167.hIgG1.NG2LH and gCDX-301. Data shown are the average±SD of triplicate values. Data were normalized to 10 ug/mL hFLT3L.P167.hIgG1.NG2LH as the maximum (100%) response. FIG. 4B shows EC50 potency of hFLT3L.P167.hIgG1.NG2LH and gCDX-301. Results are shown from 5 independent experiments with lines marking the mean±SEM.

DETAILED DESCRIPTION OF EMBODIMENTS OF THE INVENTION

I. DEFINITIONS

Figure 1:
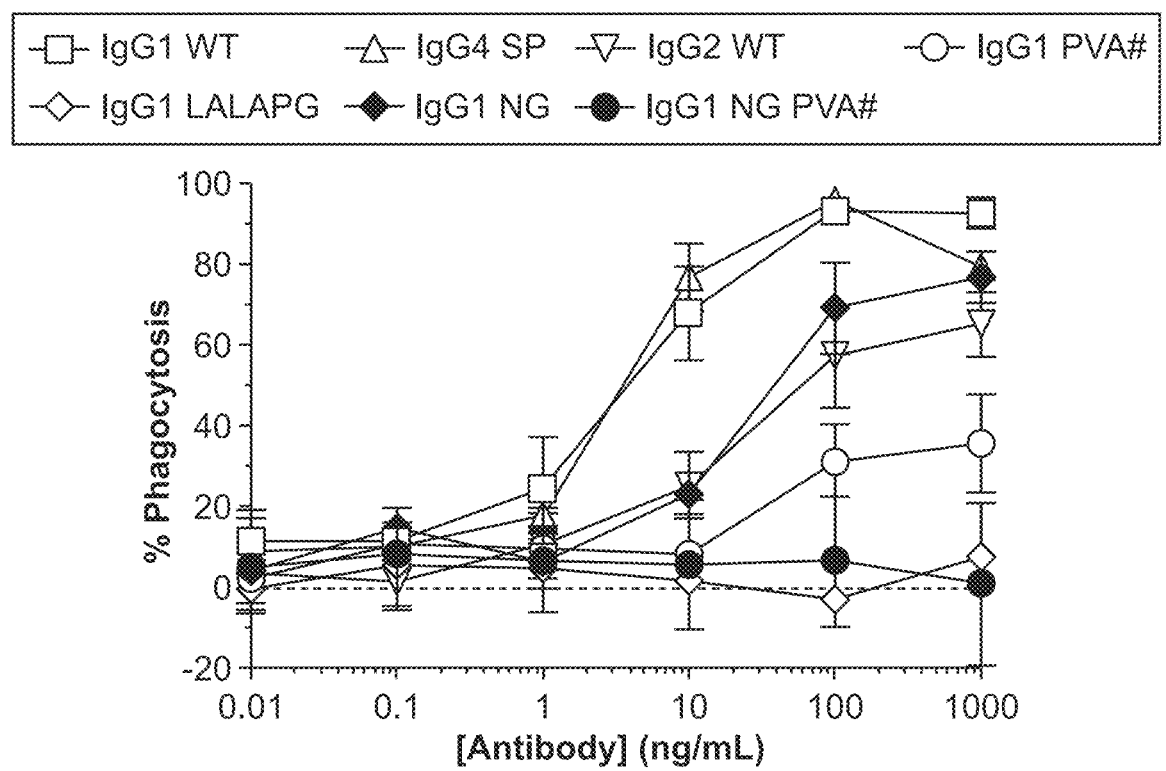
FIG. 1 shows different levels of ADCP activity by anti-Her2 antibodies with a wildtype or variant Fc domain. Primary M1 macrophages were incubated with SkBr3 target cells. The x-axis shows antibody concentration and the y-axis shows percent phagocytosis.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "Flt3 ligand" also referred to as "Flt3L," refers to a protein that is capable of binding the Flt3 receptor with sufficient affinity such that the protein is useful as a diagnostic and/or therapeutic agent in targeting the Flt3 receptor (Flt3R). In one embodiment, the extent of binding of a Flt3 ligand to an unrelated, non-Flt3R protein is less than about 10% of the binding of the protein to Flt3L as measured, e.g., by a radioimmunoassay (RIA). In certain embodiments, a protein that binds to the Flt3R has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M). In certain embodiments, a Flt3L binds to a Flt3R that is conserved among Flt3R from different species.

The term "Flt3L," as used herein, refers to the cleaved, soluble Flt3L (e.g., approximately residues 27-185 of SEQ ID NO:21), but may also refer to any native Flt3L from any vertebrate source, including mammals such as primates (e.g. humans) and rodents (e.g., mice and rats), unless otherwise indicated. The term can encompass "full-length," unprocessed Flt3L as well as any form of Flt3L that results from processing in the cell, e.g., removal of a signal peptide (leader sequence) or cleavage from the TM domain. The term also encompasses naturally occurring variants of Flt3L, e.g., splice variants or allelic variants. The amino acid sequence of an exemplary human Flt3L with the endogenous signal sequence is shown in SEQ ID NO:21 and is also provided in GenBank Accession Record P49771, while in other embodiments, the amino acid sequence of mature Flt3L protein without an exogenous leader sequence is provided as residues 27-167 of SEQ ID NO:21. Minor sequence variations especially conservative amino acid substitutions of Flt3L that do not affect Flt3L's function and/or activity (e.g., binding to Flt3 receptor (GenBank Acc. No. NP_004110) are also contemplated by the invention.

The term "Flt3L-Fc fusion protein" or alternatively, "Fc-effectorless Flt3L-Fc fusion protein," as used herein refers to a fusion protein in which a Flt3L polypeptide is linked, directly or indirectly, to a variant IgG Fc region wherein the variant Fc region has attenuated effector function relative to its counterpart wildtype Fc region. It is noted that for any use of the term "effectorless Flt3L-Fc fusion protein" the term "effectorless" applies to the Fc portion of the fusion protein. In certain preferred embodiments, the Flt3L-Fc fusion protein of the invention comprises a human Flt3L protein or polypeptide linked to a human IgG Fc region. In certain embodiments, the human Flt3L protein comprises the amino acid sequence of SEQ ID NO:22. However, it is understood that minor sequence variations such as insertions, deletions, substitutions, especially conservative amino acid substitutions of Flt3L or Fc that do not significantly affect the function and/or activity of Flt3L or of an effectorless Flt3L-Fc fusion protein of the invention (e.g., SEQ ID NO:26) are also contemplated by the invention. The effectorless Flt3L-Fc fusion protein of the invention can bind to the Flt3 receptor protein (Flt3), which can lead to Flt3 receptor downstream signaling. As used herein, CDX-301 refers to a Flt3L having the amino acid sequence of SEQ ID NO:23.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

"Effector functions" refer to those biological activities attributable to the Fc region of an antibody, an isolated Fc region, or an Fc region fused to another protein, wherein the Fc region varies with the isotype of the source antibody. Examples of antibody effector functions include: C1q binding and complement dependent cytotoxicity (CDC); Fc receptor binding; antibody-dependent cell-mediated cytotoxicity (ADCC); phagocytosis; antibody dependent cellular phagocytosis (ADCP); down regulation of cell surface receptors (e.g. B cell receptor); and B cell activation. In certain embodiments, the Flt3L-Fc fusion protein does not exhibit any effector function or any detectable effector function. In certain other embodiments, the Flt3L-Fc fusion protein exhibits substantially reduced effector function, e.g., about 50%, 60%, 70% 80%, or 90% reduced effector function relative to a fusion protein comprising a Flt3L protein of the present invention fused to a wildtype Fc protein having SEQ ID NO:12.

"Dendritic cell expansion," "expansion of dendritic cells," or "increase in the number of dendritic cells" as used herein refers to an increase in the number of dendritic cells in an in vitro assay or as measured in an in vivo experiment.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" protein or polypeptide is one which has been separated from a component of its natural environment. In some embodiments, a protein is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a Flt3L-Fc fusion protein" refers to one or more nucleic acid molecules encoding a Flt3L-Fc fusion protein, including such nucleic acid molecule(s) in a single vector or separate vectors, and such nucleic acid molecule(s) present at one or more locations in a host cell.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, fusion proteins of the invention are used to delay development of a disease or to slow the progression of a disease.

The phrase "therapeutically effective amount" means an amount of a protein of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the therapeutic agent or a combination of agents as described herein may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the therapeutic agent or a combination of agents as described herein may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" as used herein refer to or describe the physiological condition in mammals that is typically characterized by unregulated cell growth. A "tumor" comprises one or more cancerous cells. Tumors include solid and liquid tumors. Examples of cancer include, but are not limited to, carcinoma, lymphoma, blastoma, sarcoma, myeloma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, malignant brain tumors, melanoma, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, as well as acute myelogenous leukemia (AML).

The term "cold tumor" or "immune desert" as used herein refers to a cancerous tumor which is hypo-immunogenic or characterized by insufficient elicitation of tumor-specific immunity and resistance to immunogenic cytotoxicity.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. COMPOSITIONS AND METHODS

A. The Effectorless Fc Protein

In one aspect, the invention provides a novel effectorless IgG1 Fc protein that has surprisingly reduced effector activity. The Fc protein designed and described herein comprises the amino acid sequence of SEQ ID NO:2 and is also referred to herein as "FcNG2LH" or "Fc NG PVA#." As shown herein, the FcNG2LH Fc protein has significantly reduced ADCP activity compared to proteins having a wildtype IgG1 Fc domain (see, e.g., at least in Examples 1 and 10), as well as reduced activation of cytokine release by macrophages (see, e.g., Example 1) and reduced ADCC activity. Also notable is the surprising increase in thermostability of the FcNG2LH protein relative to the thermostability of an IgG1 Fc domain containing only the N297G mutation.

The design of an effectorless IgG1 Fc domain protein has utility in the context of many therapeutic molecules, in addition to its use in an Flt3L-Fc fusion protein as described herein. For example, antibodies designed to bind to and activate a molecule (e.g., cell surface receptor) by bridging two or more of the molecules together, antibodies that target checkpoint inhibitors, bi- or multispecific antibodies that have at least one arm that binds to and induces ADCC and/or ADCP activity. The ordinarily skilled artisan will appreciate the use of the effectorless Fc protein described herein for the generation of a fusion protein wherein the effectorless Fc protein is linked (e.g., via an amino acid bond) to the N-terminus and/or C-terminus of a second protein to the C-terminus and/or N-terminus of the effectorless Fc protein, respectively. The second protein is preferably one which has a desired therapeutic function. Effectorless Fc domains can prevent adverse reactions such as neutrophilia caused by binding of an IgG Fc receptor. There is need in the field of therapeutic proteins to continually develop ways to refine the control of Fc effector functions.

In one aspect, the invention provides antibodies in which the heavy chain constant domain comprises the FcNG2LH protein of SEQ ID NO:2. In some embodiments, the Flt3L-Fc fusion proteins described herein include immunoglobulins and antibodies. Persons having ordinary skill in the art can readily envision the format of a variety of antigen-specific antibodies which can accommodate and benefit from the presence of the NG2LH mutations and resultant lack of or decrease in effector function. For example, the human IgG1 FcNG2LH of the present disclosure could be part of a monoclonal antibody, human antibody, chimeric antibody, a humanized antibody, a bispecific antibody, or a multispecific antibody. In other words, any immunoglobulin structure that includes or can include an IgG1 Fc domain.

B. Exemplary Flt3L-Fc Fusion Proteins

In one aspect, the invention provides Flt3L-Fc fusion proteins that bind to the Flt3 receptor (Flt3R) and wherein the Fc protein has approximately no effector function or has greatly reduced effector function as compared to the wild-type Fc protein. These fusion proteins are useful for treatment of cancer through a variety of cancer immunotherapy treatment protocols, especially in cases where a patient either does not respond to checkpoint inhibitor immuno-therapy or has a limited response to checkpoint inhibitor immunotherapy. It is thought that a lack of anti-tumor immune response in a "cold tumor" or "immune desert" is at least in part due to insufficient or a lack of anti-tumor T cell response. An effective anti-tumor T cell response requires cross presentation of tumor antigens by dendritic cells (DCs).

Accordingly, one means of increasing efficacy of cancer immunotherapy is to increase the number of antigen-presenting DCs within a tumor. It is well known that Flt3L functions in part to increase DCs in a subject, through proliferation, differentiation, development and mobilization of progenitor cells. While there is evidence that a Flt3L protein administered to a healthy subject can indeed expand DCs and hematopoietic stem cells (e.g., Anandasabapathy et al., 2015, Bone Marrow Transplant., 50:924-930) one concern is the relatively short half-life of recombinant Flt3L in the blood which may result in less therapeutic efficacy and/or a need for too frequent dosing.

A well-established strategy to extend the serum half-life of a therapeutic protein is to link or fuse it to an immunoglobulin Fc domain (e.g., via a peptide bond, preferably at the N-terminus of the Fc protein) (e.g., Czajkowsky et al., 2012, EMBO, 4:1015-1028; Ha et al., 2016, Front Immunol, 7:394). However, in the case of a Flt3L-Fc fusion protein for use in, e.g., cancer immunotherapy, it may be disadvantageous to have a functional Fc domain which may activate many and unpredictable immunologic or inflammatory processes in situ. Indeed, it's important to minimize risk of administration resulting in a cytokine storm or cytokine release syndrome (CRS). Additionally, interaction between a wildtype Fc of a Flt3L-Fc fusion protein domain and a Fc receptor on an immune effector cell may lead to phagocytic destruction of the DC bound by the Flt3L-Fc fusion protein. It can be important to minimize and thereby control for effects of the Fc region of the Flt3L-Fc fusion protein while maintaining the advantages imparted by the Fc region. Described herein is a new effectorless IgG Fc region, referred to herein as "Fc-NG2LH" or "Fc-PVA# N297G," which was shown to have surprisingly low effector function (see, e.g., Example 7), especially when compared to, e.g., wildtype IgG1 Fc, IgG1 Fc-N297G, and IgG4 Fc regions. Moreover, as shown in Example 8, introduction of the NG2LH variant resulted in an unpredicted increase in the thermostability of the Fc domain as well as effects on half-life in the serum of an animal.

Additional characterization of Flt3L-Fc fusion protein variants show that substituting Flt3L W144 significantly increases immunogenicity as determined in an in vitro T cell proliferation assay, suggesting removing a potential oxidation liability at position 149 of Flt3L (SEQ ID NO:21) could be detrimental to a therapeutic effectorless Flt3L-Fc fusion protein product. In contrast, however, Example 9 shows substitution of potential glycosylation sites at positions 149 and 151 did not increase immunogenicity as determined by the in vitro T cell proliferation assay, suggesting that mutations at these and other positions may be amenable to manufacture of a Flt3L-Fc fusion protein.

Importantly, in vivo administration of varying doses of an effectorless Flt3L-Fc fusion protein as disclosed herein produced a large expansion of dendritic cells (e.g., see Example 5). Moreover, the level of DC expansion is arguably much greater than what has been observed with an equivalent dose of CDX-301.

The Flt3L-Fc fusion protein comprises a Flt3 ligand (Flt3L) protein linked to an IgG1 Fc region wherein the IgG1Fc has reduced or no effector function relative to the same Flt3L fused to a wildtype IgG1 Fc Fc. The Flt3L portion of the Flt3L-Fc fusion protein can bind to the cell surface Flt3 receptor (Flt3R). A sequence of the Flt3L protein is described in GenBank Accession No. P49771 (provided herein as SEQ ID NO:21) as a protein 235 amino acids in length, with the signal peptide extending from approximately residues 1-26 and a transmembrane domain extending approximately from residues 185-205. Residues 29-159 are described in the GenBank record as the Flt3 ligand, while Savvides et al. (Nat Struct Bio, 7:486-491) state that residues 27-160 alone have been shown to be sufficient for bioactivity. In some embodiments, the present disclosure envisions Flt3 ligand domains which comprise residues of SEQ ID NO:21 with a N-terminus being any amino acid residue from 24 to 30 of SEQ ID NO:21 and a C-terminus being any amino acid residue at position 167-190 of SEQ ID NO:21. While Savvides et al. (ibid) showed that a polypeptide comprising residues 27-160 alone (and configured as a dimer) is sufficient for functional activity of the ligand, studies described in Example 2 below show that using a Flt3L protein which terminates N-terminal to residue 167 of SEQ ID NO:21, e.g., is covalently linked to the Fc N-terminal residue (of SEQ ID NO:13). It is understood that variants of Flt3L are also envisioned in the present disclosure, such as mature Flt3L proteins comprising a protein sequence having at least 75%, 80%, 85%, 90%, 91%, 92%, 93%, 94%, 95%, 96%, 97%, 98% or 99% identity to SEQ ID NO:21 residues 27-167. It shown here (e.g., Example 3 below) that the fragment size of Flt3 which is fused to an Fc protein can have a significant impact on aggregation of the fusion protein.

In one aspect, the invention provides a Flt3L-Fc fusion protein comprising a Flt3L protein comprising an amino acid sequence which is at least 95% identical to residues 27-167 of SEQ ID NO:21 and an IgG Fc molecule which is at least 95% identical to SEQ ID NO:13. The IgG Fc molecule has attenuated Fc effector function relative to a wildtype IgG1 Fc polypeptide (SEQ ID NO:12), wherein the Fc effector function is selected from CDC, ADC, ADCC, and/or ADCP. In some embodiments, the IgG Fc molecule has attenuated ADCP activity relative to the wildtype IgG1 Fc polypeptide. Without being bound by theory, it is considered that the low to absent effector function of the Fc(NG2LH) protein is due to the presence of unique combination of both the N297G mutation (at position 76 of SEQ ID NO:13) and amino acids PVAGP (residues 13-17 of SEQ ID NO:13) in the lower hinge of the Fc(NG2LH) protein.

a) Substitution, Insertion, and Deletion Variants

In certain embodiments, protein variants having one or more amino acid substitutions are provided. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an fusion protein of interest and the products screened for a desired activity, e.g., decreased immunogenicity or decreased ADCP.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a Flt3L-Fc fusion protein with an N-terminal methionyl residue. Other insertional variants of the Flt3L-Fc fusion protein molecule include the fusion to the N- or C-terminus of the Flt3L-Fc fusion protein to an enzyme (e.g. for ADEPT) or a polypeptide which increases the serum half-life of the Flt3L-Fc fusion protein.

b) Glycosylation Variants

In certain embodiments, a Flt3L-Fc fusion protein provided herein is altered to increase or decrease the extent to which the Fc portion of the Flt3L-Fc fusion protein is glycosylated. Addition or deletion of glycosylation sites to Fc domain may be conveniently accomplished by altering the amino acid sequence such that one or more glycosylation sites is created or removed.

With respect to a Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a Flt3L-Fc fusion protein of the invention may be made in order to create effectorless Fc variants with certain improved properties.

In one embodiment, Fc fusion variants are provided having a carbohydrate structure that lacks fucose attached (directly or indirectly) to the Fc region. For example, the amount of fucose may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Fc variants are further provided with bisected oligosaccharides, e.g., in which a biantennary oligosaccharide attached to the Fc region of the fusion protein is bisected by GlcNAc. Such Fc variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Flt3L-Fc fusion protein variants with at least one galactose residue in the oligosaccharide attached to the Fc region are also provided. Such Flt3L-Fc fusion proteins (and therefore Fc) variants may have improved CDC function. Such antibody variants are described, e.g., in WO 1997/30087 (Patel et al.); WO 1998/58964 (Raju, S.); and WO 1999/22764 (Raju, S.).

c) Protein Derivatives

In certain embodiments, an effectorless Fc protein, an antibody or a fusion protein comprising the effectorless Fc protein, or Flt3L-Fc fusion protein provided herein may be further modified to contain additional nonproteinaceous moieties that are known in the art and readily available. The moieties suitable for derivatization of the Flt3L-Fc fusion protein include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the Fc-fusion protein may vary, and if more than one polymer are attached, they can be the same or different molecules. In general, the number and/or type of polymers used for derivatization can be determined based on considerations including, but not limited to, the particular properties or functions of the Flt3L-Fc fusion protein to be improved, whether the Flt3L-Fc fusion protein derivative will be used in a therapy under defined conditions, etc.

In another embodiment, conjugates of a Flt3L-Fc fusion protein and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the fusion protein-nonproteinaceous moiety are killed.

C. Recombinant Methods and Compositions

Flt3L fusion proteins may be produced using recombinant methods and compositions readily known to the ordinarily skilled artisan. In one embodiment, isolated nucleic acid encoding a Flt3L-Fc fusion protein described herein is provided. Such nucleic acid may encode an amino acid sequence comprising the Flt3L and Fc portions of the Flt3L-Fc fusion protein. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes a Flt3L polypeptide and an Fc polypeptide according to the present invention. In preferred embodiments, the nucleic acid encoding the Flt3L polypeptide is upstream of the nucleic acid encoding the Fc polypeptide. Moreover, the 2 nucleic acids are in a single operon. In one embodiment, the host cell is eukaryotic, e.g. a Chinese Hamster Ovary (CHO) cell or lymphoid cell (e.g., Y0, NS0, Sp20 cell). In one embodiment, a method of making a Flt3L-Fc fusion protein is provided, wherein the method comprises culturing a host cell comprising a nucleic acid encoding the Flt3L-Fc fusion protein, as provided above, under conditions suitable for expression of the Flt3L-Fc fusion protein, and optionally recovering the Flt3L-Fc fusion protein from the host cell (or host cell culture medium).

For recombinant production of a Flt3L-Fc fusion protein, nucleic acid encoding a Flt3L-Fc fusion protein, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the fusion protein).

Suitable host cells for cloning or expression of effectorless Fc proteins, antibodies or fusion proteins containing the Fc protein, or e.g., Flt3L-Fc fusion protein-encoding vectors include prokaryotic or eukaryotic cells described herein. For example, Flt3L-Fc fusion proteins may be produced in bacteria, in particular when glycosylation and Fc effector function are not needed. For expression of polypeptides in bacteria, see, e.g., U.S. Pat. Nos. 5,648,237, 5,789,199, and 5,840,523. (See also Charlton, *Methods in Molecular Biology*, *Vol.* 248 (B. K. C. Lo, ed., Humana Press, Totowa, N.J., 2003), pp. 245-254, describing expression of antibody fragments in *E. coli*.) After expression, the Flt3L-Fc fusion protein may be isolated from the bacterial cell paste in a soluble fraction and can be further purified.

In addition to prokaryotes, eukaryotic microbes such as filamentous fungi or yeast are suitable cloning or expression hosts for a Flt3L-Fc fusion protein-encoding vectors, including fungi and yeast strains whose glycosylation pathways have been "humanized," resulting in the production of a Flt3L-Fc fusion protein with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated Flt3L-Fc fusion protein are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

D. Assays

Flt3L-Fc fusion proteins which can facilitate expansion of DCs as provided herein may be identified, screened for, or characterized for their physical/chemical properties and/or biological activities by various assays known in the art.

E. Immunoconjugates

The invention also provides immunoconjugates comprising a Flt3L-Fc protein herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate of the Flt3L-Fc protein is generated in a manner similar to generation of an antibody-drug conjugate (ADC) in which an antibody is conjugated to one or more drugs, including but not limited to a maytansinoid (see U.S. Pat. Nos. 5,208,020, 5,416,064 and European Patent EP0425235B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises a Flt3L-Fc protein as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises a Flt3L-Fc protein as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of a Flt3L-Fc protein and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

F. Pharmaceutical Formulations

Pharmaceutical formulations of a Flt3L-Fc fusion protein as described herein are prepared by mixing such protein having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation herein may also contain more than one active ingredients as necessary for the particular indication being treated, preferably those with complementary activities that do not adversely affect each other. For example, it may be desirable to further provide a dendritic cell maturation factor and/or adjuvant. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the Fc fusion protein, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the Flt3L-Fc proteins provided herein may be used in therapeutic methods. In one aspect, a Flt3L-Fc protein for use as a medicament is provided. In further aspects, a Flt3L-Fc protein for use in a cancer is provided. In certain embodiments, a Flt3L-Fc protein for use in a method of treatment is provided. In certain embodiments, the invention provides a Flt3L-Fc protein for use in a method of treating an individual having cancer comprising administering to the individual an effective amount of the Flt3L-Fc protein. In one such embodiment, the method further comprises administering to the individual an effective amount of at least one additional therapeutic agent, e.g., as described below. In further embodiments, the invention provides a Flt3L-Fc protein for use in expanding dendritic cells. In certain embodiments, the invention provides a Flt3L-Fc protein for use in a method of expanding dendritic cells in an individual comprising administering to the individual an effective amount of the Flt3L-Fc protein to expand dendritic cells. An "individual" according to any of the above embodiments is preferably a human.

In a further aspect, the invention provides for the use of a Flt3L-Fc protein in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. In a further embodiment, the medicament is for expanding dendritic cells. In a further embodiment, the medicament is for use in a method of expanding dendritic cells in an individual comprising administering to the individual an amount effective of the medicament to expand dendritic cells. An "individual" according to any of the above embodiments may be a human.

In a further aspect, the invention provides a method for treating a cancer. In one embodiment, the method comprises administering to an individual having such cancer an effective amount of a Flt3L-Fc protein. In one such embodiment, the method further comprises administering to the individual an effective amount of at least one additional therapeutic agent, as described below. An "individual" according to any of the above embodiments may be a human.

In a further aspect, the invention provides a method for expanding dendritic cells in an individual. In one embodiment, the method comprises administering to the individual an effective amount of a Flt3L-Fc protein to expand dendritic cells. In one embodiment, an "individual" is a human.

In a further aspect, the invention provides pharmaceutical formulations comprising any of the a Flt3L-Fc proteins provided herein, e.g., for use in any of the above therapeutic methods. In one embodiment, a pharmaceutical formulation comprises any of the a Flt3L-Fc proteins provided herein and a pharmaceutically acceptable carrier. In another embodiment, a pharmaceutical formulation comprises any of the Flt3L-Fc proteins provided herein and at least one additional therapeutic agent, e.g., as described below.

Flt3L-Fc proteins of the invention can be used either alone or in combination with other agents in a therapy. For instance, a Flt3L-Fc protein of the invention may be co-administered with at least one additional therapeutic agent.

Such combination therapies noted above encompass combined administration (where two or more therapeutic agents are included in the same or separate formulations), and separate administration, in which case, administration of the Flt3L-Fc protein of the invention can occur prior to, simultaneously, and/or following, administration of the additional therapeutic agent or agents. In one embodiment, administration of the Flt3L-Fc protein and administration of an additional therapeutic agent occur within about one month, or within about one, two or three weeks, or within about one, two, three, four, five, or six days, of each other. Flt3L-Fc proteins of the invention can also be used in combination with radiation therapy.

A Flt3L-Fc fusion protein of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Flt3L-Fc fusion proteins of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The Flt3L-Fc fusion protein need not be, but is optionally formulated with one or more agents currently used to prevent or treat the disorder in question. The effective amount of such other agents depends on the amount of Flt3L-Fc fusion protein present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a Flt3L-Fc fusion protein of the invention (when used alone or in combination with one or more other additional therapeutic agents) will depend on the type of disease to be treated, the type of Flt3L-Fc fusion protein, the severity and course of the disease, whether the Flt3L-Fc fusion protein is administered for preventive or therapeutic purposes, previous therapy, the patient's clinical history and response to the fusion protein, and the discretion of the attending physician. The Flt3L-Fc fusion protein is suitably administered to the patient at one time or over a series of treatments. Depending on the type and severity of the disease, about 1 µg/kg to 15 mg/kg (e.g. 0.1 mg/kg-10 mg/kg) of Flt3L-Fc fusion protein can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the Flt3L-Fc fusion protein would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful.

It is understood that any of the above formulations or therapeutic methods may be carried out using an immunoconjugate of the invention in place of or in addition to a Flt3L-Fc fusion protein.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a Fc fusion protein of the invention. The label or package insert indicates that the composition is used for treating the condition of choice. Moreover, the article of manufacture may comprise (a) a first container with a composition contained therein, wherein the composition comprises a Fc fusion protein of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a Flt3L-Fc fusion protein.

III. EXAMPLES

The following are examples of methods and compositions of the invention. It is understood that various other embodiments may be practiced, given the general description provided above.

Example 1. Design of an Effectorless Fc Protein

The term "NG2LH" refers to a human IgG1 Fc domain that comprises the IgG1 N297G substitution and that "swaps" the lower hinge residues 233-236 (ELLG, SEQ ID NO:19) of IgG1 with residues 233-236 (PVA; no amino acid at position 236, also referred to herein as "PVA#") of human IgG2, wherein positions are numbered according to the EU index as described in Kabat. The effectorless nature of the NG2LH Fc variant protein (also referred to herein as "PVA# NG") was first shown in the context of a full-length antibody and in comparison to wildtype, N297G and other Fc variant IgG1's, as well as IgG2 and IgG4 antibodies, as defined in Table 2 below.

TABLE 2

| SEQ ID NO: | Description of Heavy Chain Constant Region (CH1-CH3) | Substitution(s) (EU Numbering) |
|---|---|---|
| 2 | IgG1 NG2LH, aka IgG1 NG PVA# | N297G/E233P/L234V/L235A/G236# |
| 3 | IgG1 NG | N297G |
| 4 | IgG1 PVA# | E233P/L234V/L235A/G236# |
| 5 | IgG1 NG PVA# G | N297G/E233P/L234V/L235A/G236#/A327G |
| 6 | IgG1 NG PVA# GSS | N297G/E233P/L234V/L235A/G236#/A327G/A330S/P331S |
| 7 | IgG1 PG | P329G |

TABLE 2-continued

| SEQ ID NO: | Description of Heavy Chain Constant Region (CH1-CH3) | Substitution(s) (EU Numbering) |
|---|---|---|
| 8 | IgG1 LALA | L234A/L235A |
| 9 | IgG1 LALAPG | L234A/L235A/P329G |

Full length antibodies comprising the heavy chain constant regions (CH1-CH3) listed in Table 2 were constructed that encoded the light chain and heavy chain variable and domains of an anti-Her2 antibody (trastuzumab (HERCEPTIN®, Genentech, Inc., South San Francisco, Calif., USA) (also referred to in U.S. Pat. No. 6,407,213 and Lee et al., J. Mol. Biol. (2004), 340(5):1073-93; herein as SEQ ID NO:47). The light chain for these anti-Her2 antibodies comprised a native human C kappa constant region. Nucleic acids encoding the full length light chain and various full length heavy chains were cloned into the pRK mammalian expression vector (Eaton et al., 1986, Biochemistry 25:8343-47). Light and heavy chain nucleic acid vectors were co-expressed in CHO cells, and the antibodies were purified via protein A affinity chromatography followed by size exclusion chromatography.

The antibodies were then tested for their effects on antibody-dependent cellular phagocytosis (ADCP) and antibody-dependent cytokine release (ADCR) using primary macrophages and SK-BR-3 human breast cancer cell line that overexpresses Her2 (ATCC® HTB-30). An anti-gD antibody was used as a negative control antibody. Monocytes were isolated from donor PBMCs and stimulated with 25 ng/ml human MCSF-1 and allowed to differentiate to macrophages for 5-7 days in T-175 tissue culture flasks. The day before the ADCP and cytokine release experiments, all macrophages were stimulated with 50 ng/ml IFNγ (R&D Systems 285-IF-100/CF) to differentiate to M1 macrophages. Macrophages and SK-BR-3 GFP cells were harvested by accutase (Millipore SCR005) treatment. Dislodged macrophages and SK-BR-3 cells were resuspended in media (X-Vivo 10; Lonza 04-743Q, 10% HI FBS; Gibco 10438-026) at concentration of $2 \times 10^6$ and $0.5 \times 10^6$ cells/ml, respectively. A 96-well plate map was designed to determine the test conditions (antibody variants and treatment concentration). 2× serial dilutions of each of the antibody variants were prepared in media (6 points 10-fold dilution series: 2000, 200, 20, 2, 0.2, 0.02 ng/ml). Following the plate map, 50 ul of macrophage and 50 ul of SK-BR-3 were added to each well, resulting in 100 k macrophages and 25 k SK-BR-3 cells in each well. 100 uL of the 2× antibody serial diluted solution were combined the well of 96-well plates according to the plate map. The final antibody treatment concentrations were 1000, 100, 10, 1, 0.1, 0.01 ng/ml. 100 uL of media was added to 3 wells containing the macrophages and SK-BR-3 cells as "media only" control treatment. The 96-well plate was centrifuged at 20×g for 2 min then incubated at 37° C. for about 24 h. Cells were centrifuged at 400×g for 4 min and supernatant was collected for ADCR analyzed by Luminex Reader Millipore Multiplex. Cells were dislodged from the wells by accutase treatment. Cells in each well were washed once with 200 ul of FACS Buffer (BD, 554657). Staining solution was prepared with anti-CD11b (BD, 555385) and anti-CD14 (BD, 555396) conjugated with Alexa 647 (Invitrogen, Alexa Fluor 647 Antibody Labeling Kit, A20186) (1:100 antibody conjugate in FACS buffer). 50 uL of the staining solution were added to all the wells and incubate at 4° C. for 30-60 min. Cells were washed twice with FACS Buffer (200 ul per well). Cells in each well were resuspended in 50 ul of FACS Buffer. One plate of cells was analyzed by FACS for ADCP efficiency. FACS data were analyzed with software FlowJo. Cells were gated in the Forward and Side Scatter plot then plotted on GFP-expression on Y-axis and Alexa 647 on the X-axis. Cell percentage in each quadrant were calculated. SK-BR-3 cells were largely in quadrant 1 (Q1, GFP positive) and macrophages were largely in quadrant 3 (Q3, Alexa 647 positive). % Phagocytosis of each well were calculated:

% Phagocytosis=100%−(Q1 of each well)/(average Q1 of 3 media only control wells)

% Phagocytosis of the antibody variants with respect to the antibody treatment concentration plotted on a graph.

Two plates were analyzed by Luminex (Luminex Corp). As shown in FIG. 1, approximately no phagocytosis was observed in the presence of increasing concentrations of the LALAPG or NGLH2 Fc anti-Her2 antibodies. The highest levels of ADCP were observed with the IgG1 wildtype and IgG4 antibody variants. Intermediate levels of phagocytosis were observed for IgG2 wildtype Fc and IgG1 PVA# Fc. Accordingly, FIG. 1 shows that the IgG1 NG2LH and IgG1 LALAPG Fc domains lack ADCP activity in an in vitro assay. The experiment shows a similar lack of ADCP activity in the presence of IgG1 NG PVAG and IgG1 NG PVA# GSS (data not shown).

Results of the cytokine release profiles from the ADCP assay are provided in FIGS. 2A-2J. Consistent with the phagocytosis data, these results demonstrate that in contrast to native IgG1, IgG4, and to a lesser extent N297G, the NG2LH variant mediates no ADCR by macrophages in the presence of target cells.

Figure 2F:
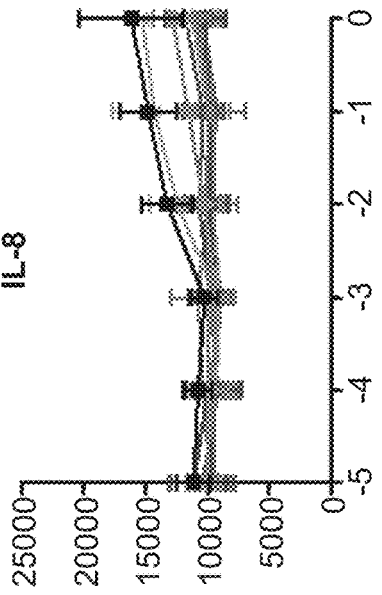
FIGS. 2F-2J show cytokine release by macrophages when the anti-Her2 antibodies with a wildtype or variant Fc domain are incubated with primary M1 macrophages and SkBr3 target cells. The x-axis shows antibody concentration and the y-axis shows pg/ml cytokine.
Figure 2G:
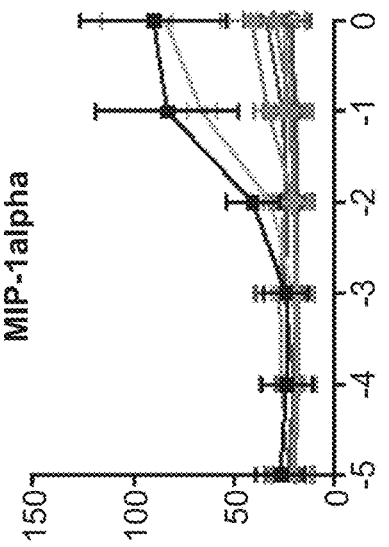
Figure 2H:
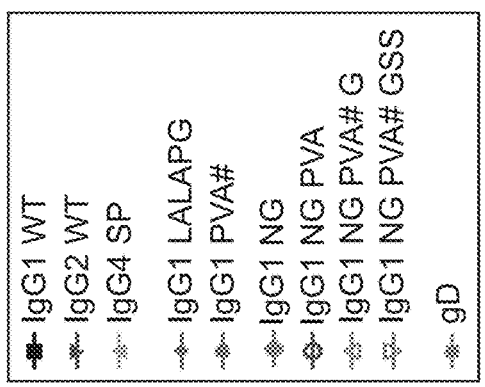
Figure 2H:
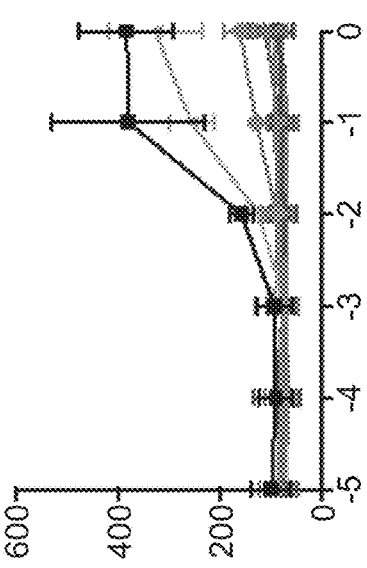
Figure 2I:
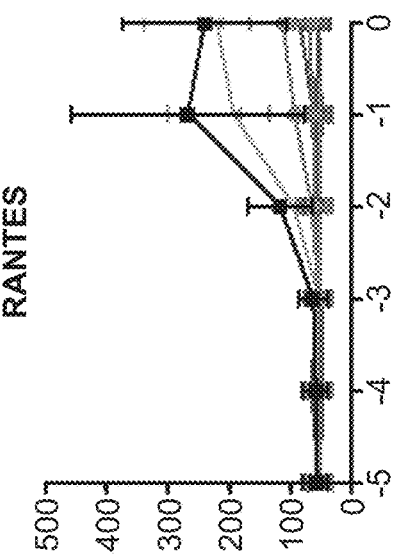
Figure 2J:
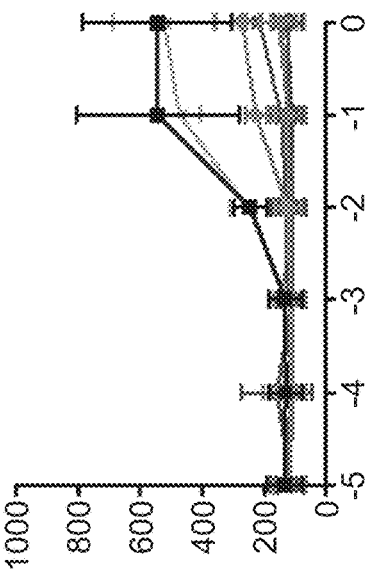
Figure 2K:
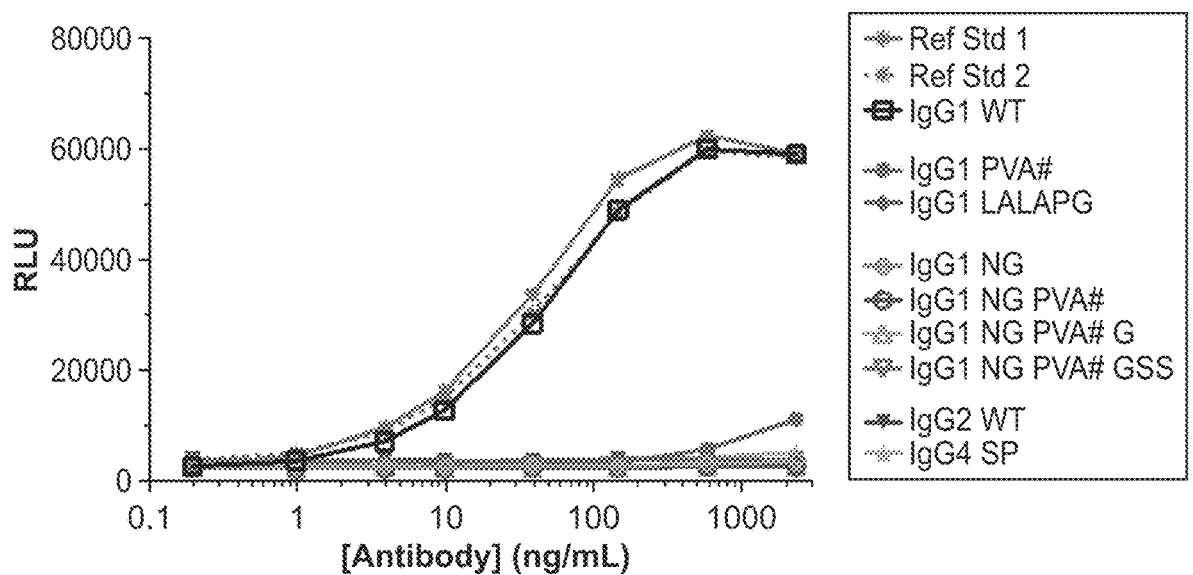
FIG. 2K shows ADCC activity of an anti-CD20 antibody having wildtype and variant Fc proteins.
Figure 2L:
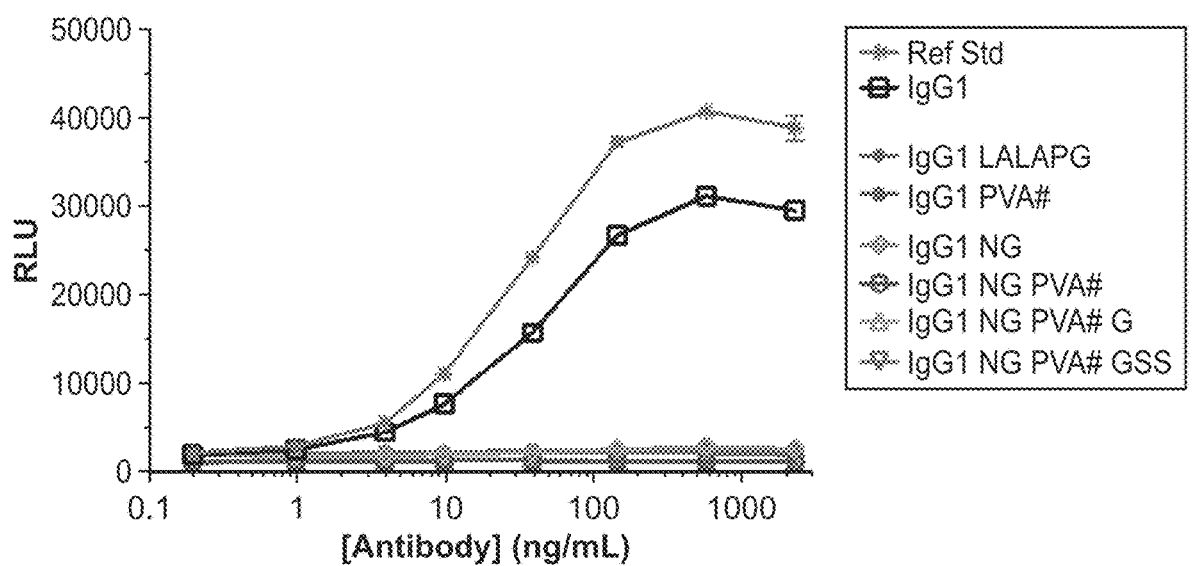
FIG. 2L shows ADCC activity of an anti-Her2 antibody having wildtype and variant Fc proteins.

These data contrast to data from an ADCC reporter assay of the variants compared to wildtype IgG1 Fc. The variable domains from ocrelizumab (anti-CD20) or trastuzumab (anti-Her2) were fused to the wildtype and variant domains described above and tested in an ADCC assay. In this assay, a NK cells was engineered as a NFAT-RE-Luciferase reporter cell, reading out RcγRIIIa binding, then assayed in the presence of WIL2S CD20+ cells or SkBr3 Her2+ cells. For both the anti-CD20 and anti-Her2 constructs with wildtype or variant domains, all non-wildtype Fc molecules had minimal activity as compared to wildtype IgG1 Fc (see FIGS. 2K and 2L).

Example 2. Design of Flt3L Fc Fusion Proteins

The Flt3L-Fc fusion proteins were generated using routine nucleic acid cloning, protein expression and protein purification techniques.

PCR was used to amplify cDNA containing the nucleotide sequence encoding the Flt3L and Fc portions of desired chimeric Flt3L-Fc proteins (see Table 3, SEQ ID NOS:10-31). For expression and production of the Flt3L-Fc proteins described in Table 3 (sequences provided in Tables 10A and 10B), the cDNA was generated to include the native signal sequence of human Flt3L (residues 1-27 of GenBank Acc. No. P49771; SEQ ID NO:21). As an example, the cDNA generated for expression of the hFLT3L.P167.5aa.hinge.hIgG1.NG.PVA# protein comprised a cDNA sequence encoding the fusion protein with the Flt3L signal sequence as provided in Table 10B as SEQ ID NO:45.

TABLE 3

| SEQ ID NO: | Construct Name |
|---|---|
| 25 | hFLT3L.P168.5aa.hinge.hIgG1.NG.PVA# |
| 26 | hFLT3L.P167.5aa.hinge.hIgG1.NG.PVA# |
| 27 | hFLT3L.P167.5aa.hinge.hIgG1 |
| 28 | hFLT3L.P167.5aa.hinge.hIgG1.NG |
| 29 | hFLT3L.P167.5aa.hinge.hIgG1.PVA# |
| 30 | hFLT3L.P167.5aa.hinge.hIgG1.LALAPG |
| 31 | hFLT3L.P167.7aa.hinge.hIgG4 |
| 32 | hFLT3L.P166.5aa.hinge.hIgG1.NG.PVA# |
| 33 | hFLT3L.L165.5aa.hinge.hIgG1.NG.PVA# |
| 34 | hFLT3L.L164.5aa.hinge.hIgG1.NG.PVA# |
| 35 | hFLT3L.C158.5aa.hinge.hIgG1.NG.PVA# |
| 36 | hFLT3L.P179.hIgG1.N297G |
| 37 | hFLT3L.Q159.hIgG1.N297G |
| 38 | hFTL3L.C158.3aa.hinge.hIgG1.NG.PVA# |
| 39 | hFTL3L.C158.no.hinge.hIgG1.NG.PVA# |
| 40 | hFTL3L.D161.no.hinge.hIgG1.NG.PVA# |
| 41 | hFLT3L.S163.no.hinge.hIgG1.NG.PVA# |
| 42 | Hs_FLT3LG.M1-L165.W144D.O.pRK-5aa.hIgG1.NG2LH |
| 43 | Hs_FLT3LG.M1-L165.S151D.O.pRK-5aa.hIgG1.NG2LH |
| 44 | Hs_FLT3LG.M1-L165.S151E.O.pRK-5aa.hIgG1.NG2LH |
| 46 | Flt3L-Fc(IgG4) |

The cDNA encoding Flt3L-Fc fusions was subcloned into a mammalian expression vector pRK5 (Gorman, et al., DNA and Protein Engineering Techniques 2:1 (1990); U.S. Pat. No. 6,232,117) and expressed under the control of the CMV promoter.

Either CHO or HEK293 cells were transiently transfected with a desired expression construct, grown in the appropriate culture media 10 or 6 days, respectively, and harvested for purification.

Purification of Flt3L-Fc fusion constructs was achieved using HiTrap MabSelect SuRe affinity capture chromatography (GE), followed by Superdex 200 SEC, and finally concentration and buffer exchange via dialysis.

Example 3. Characterization of Flt3L-Fc Fusion Proteins

The fusion proteins generated as described in Example 2 were characterized in terms of susceptibility to aggregation in solution as well as reduction and loss of disulfide bonds, each of which was analyzed by SDS-PAGE (3-5 ug per well) and HPLC SEC (SuperDex 200; equilibration buffer: 200 mM arginine, 137 mM succinic acid, pH 5.0). Data from experiments performed using Flt3L-Fc fusion proteins purified from CHO cell cultures are summarized in Table 4 below with exemplary data from Flt3L-Fc fusion construct hFLT3L.S163.no.hinge.hIgG1.NG.PVA# (SEQ ID NO:41) expressed in and purified from CHO cells and HEK293 cells shown in FIGS. 3A-3C, and data from Flt3L-Fc fusion construct hFLT3L.P167.5aa.hinge.hIgG1.NG.PVA# (SEQ ID NO:26) expressed in and purified from CHO cells and HEK293 cells shown in FIGS. 3D-3F.

TABLE 4

| SEQ ID NO: | Construct | % Aggregation | Incomplete hinge disulfide |
|---|---|---|---|
| 25 | hFLT3L.P168.5aa.hinge.hIgG1.NG.PVA# | 24 | ND* |
| 26 | hFLT3L.P167.5aa.hinge.hIgG1.NG.PVA# | 26 | ND |

TABLE 4-continued

| SEQ ID NO: | Construct | % Aggregation | Incomplete hinge disulfide |
|---|---|---|---|
| 32 | hFLT3L.P166.5aa.hinge.hIgG1.NG.PVA# | 26 | + |
| 33 | hFLT3L.L165.5aa.hinge.hIgG1.NG.PVA# | 33 | ++ |
| 34 | hFLT3L.L164.5aa.hinge.hIgG1.NG.PVA# | 35 | +++ |
| 35 | hFLT3L.C158.5aa.hinge.hIgG1.NG.PVA# | 86 | ++++ |
| 38 | hFLT3L.C158.3aa.hinge.hIgG1.NG.PVA# | 90 | +++ |
| 39 | hFLT3L.C158.no.hinge.hIgG1.NG.PVA# | 77 | ++ |
| 41 | hFLT3L.S163.no.hinge.hIgG1.NG.PVA# | 85 | ++++ |

*ND = Not detected

The data analysis of the variants, summarized in Table 4 above, showed that the number of amino acid residues present between the last cysteine of the Flt3L molecule and the first cysteine of the Fc(NG2LH) molecule (junction length) can impact the level of aggregation and/or disulfide bond formation. When the junction length is less than 14 residues, up to 30% of each construct appears to lack intermolecular hinge disulfides. A junction length of 5 amino acid residues or less resulted in very high aggregation. The lowest levels of aggregation were observed for fusion proteins of SEQ ID NOS. 24, 26, 32, 33, and 34. The lowest levels of incomplete hinge disulfide bonding was observed for fusion proteins of SEQ ID NOS. 25, 26, and 32, with SEQ ID NOS. 33 and 39 also having relatively low levels of incomplete hinge disulfide. The data observed here was somewhat unexpected considering that the structures of both the Flt3L and Fc proteins are well characterized and shown to be capable of folding as independent domains. It is noted, however, that each protein domain contains cysteine residues important for disulfide bonding and structural integrity. Accordingly, the data show that design of a Flt3L-Fc (NG2LH) fusion molecule requires careful assessment of the protein product to ensure sufficient covalent Fc-dimerization and minimal or lack of aggregation.

Example 4. In Vitro Functional Assays for Flt3L Activity

In vitro assays were done to assess the functional properties of an Flt3L-Fc fusion protein compared to the function of the Flt3L protein (no Fc fusion; SEQ ID NO:23). The in vitro assay performed as described here can be used to measure the potency of a Flt3L protein to induce proliferation of a human cell line expressing Flt3 receptor.

Figure 4A:
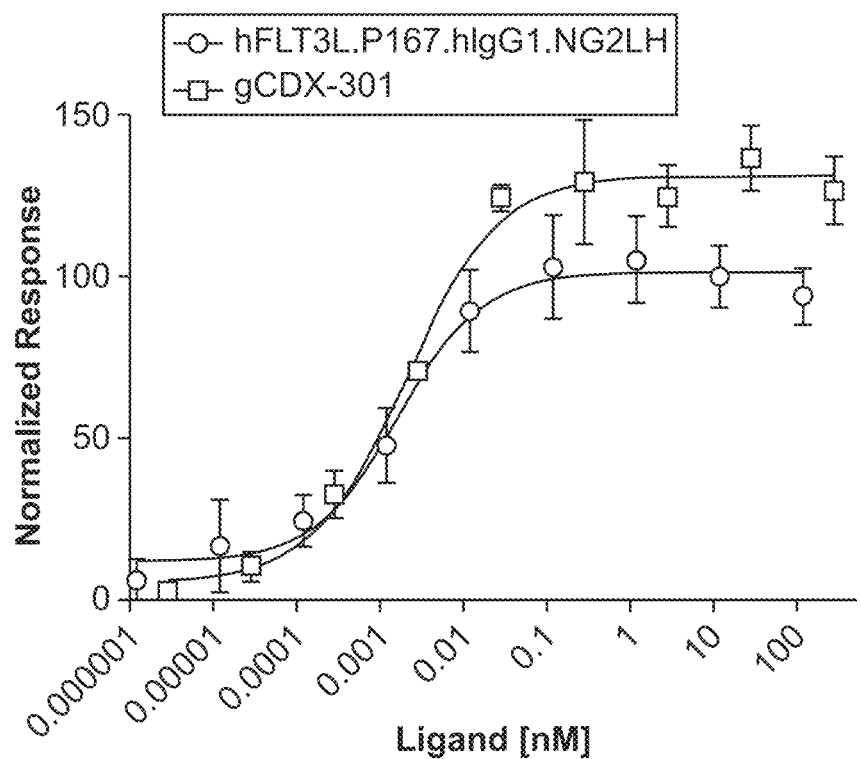
FIGS. 4A-4B shows that Flt3L induces proliferation of OCI-AMLS cells in vitro.
Figure 4B:
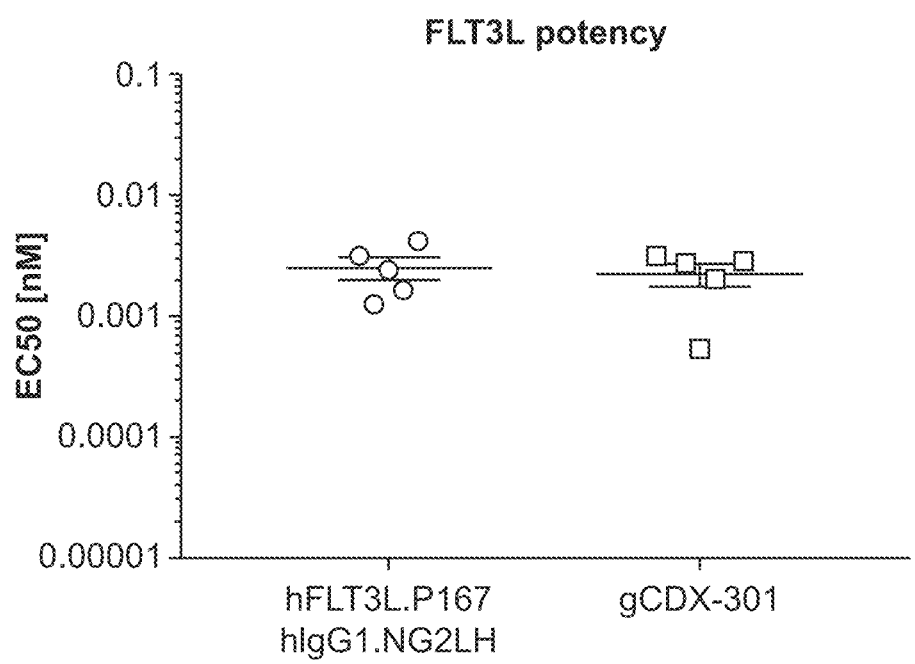

Costar 96-well flat bottom plates (Cat #3610 Thermo Fisher) were coated overnight at room temperature with 100 uL of Poly-L-ornithine (Cat #A-004-C EMD Millipore), washed 3× with PBS and allowed to dry. Human OCI-AMLS cells (No. ACC 247, DSMZ) were seeded at 3000 cells per well in 100 uL of assay media (RPMI 1640 containing 5% heat inactivated FBS, 1× Glutamax). Flt3L test articles were diluted to 20 ug/mL in assay media and serially diluted 1:10. 100 uL of diluted test article was added to each well (in triplicate) to achieve a final starting concentration of 10 ug/mL. Maximum and minimum control wells included 10 ug/mL hFLT3L.P167.hIgG1.NG2LH (SEQ ID NO:26) or assay media alone. Assay plates were incubated at 37° C., 5% $CO_2$ for 7 days. 100 uL of supernatant was removed from each well and then 100 uL of Cell Titer Glo (Cat#PR-G7572 Thermo Fisher) was added to each well and plates were incubated for 8-10 min in the dark. Luminescence was measured with a SpectraMax i3 plate reader (Molecular Devices). Raw values were normalized to the maximum and minimum control wells. A dose response of each test article was plotted with XLfit (IDBS) and EC50 values determined using a four parameter logistic curve. Graphs shown in FIGS. 4A-4B were generated with Graph-Pad Prism 7.

These data show that both hFLT3L.P167.hIgG1.NG2LH and gCDX-301 induced dose-dependent proliferation of OCI-AMLS cells in vitro. Average $EC_{50}$ potency values were comparable: 2.5±0.5 pM for hFLT3L.P167.hIgG1.NG2LH; 2.3±0.5 pM for gCDX-301. Moreover, hFLT3L.P167.hIgG1.NG2LH and gCDX-301 can induce the proliferation of OCI-AMLS cells in vitro with at least equivalent potency.

Example 5. PKPD Studies in Mouse

Given the complexities of the immune system, it can be important to show pharmacodynamics in mammalian subjects that can provide information for this human Fc molecule. PK/PD studies were performed with mice as described here.

The study was approved by Genentech's Institutional Animal Care and Use Committee and was conducted using SCID mice. Animals were divided into 3 groups. Animals in Group 1, 2, and 3 were given FLT3L-Fc (SEQ ID NO:37-Flt3L.Q159.Fc.NG) at 0.1, 1.0, and 10 mg/kg, respectively. Whole blood was collected at selected time points for cell population counts by FACS. Plasma was collected and assayed using a huFlt3L ELISA to determine the amount of test article in each sample.

Group mean PK parameters are summarized in Table 5 below.

TABLE 5

| Nominal Dose | $C_{max}$ (ug/mL) | $C_{max}$/Dose (ug/mL)/ (mg/kg) | $AUC_{inf}$ (ug/ml * day) | $AUC_{inf}$/Dose (ug/mL * day)/ (mg/kg) | CL (mL/day/ kg) |
|---|---|---|---|---|---|
| 0.1 mg/kg | 2.68 | 26.8 | 4.42 | 22.6 | 22.6 |
| 1 mg/kg | 27.9 | 27.9 | 77.9 | 77.9 | 12.8 |
| 10 mg/kg | 273 | 27.3 | 768 | 76.8 | 13 |

The NCA parameters reported in Table 5 include $C_{max}$ (Observed maximum serum concentration after the first dose); $C_{max}$/Dose (Dose normalized $C_{max}$); $AUC_{inf}$ (Area under the serum concentration–time curve from Day 0 to infinity); $AUC_{inf}$/Dose (Dose normalized AUC); and CL (Clearance calculated using the serum concentration–time curve).

Figure 5:
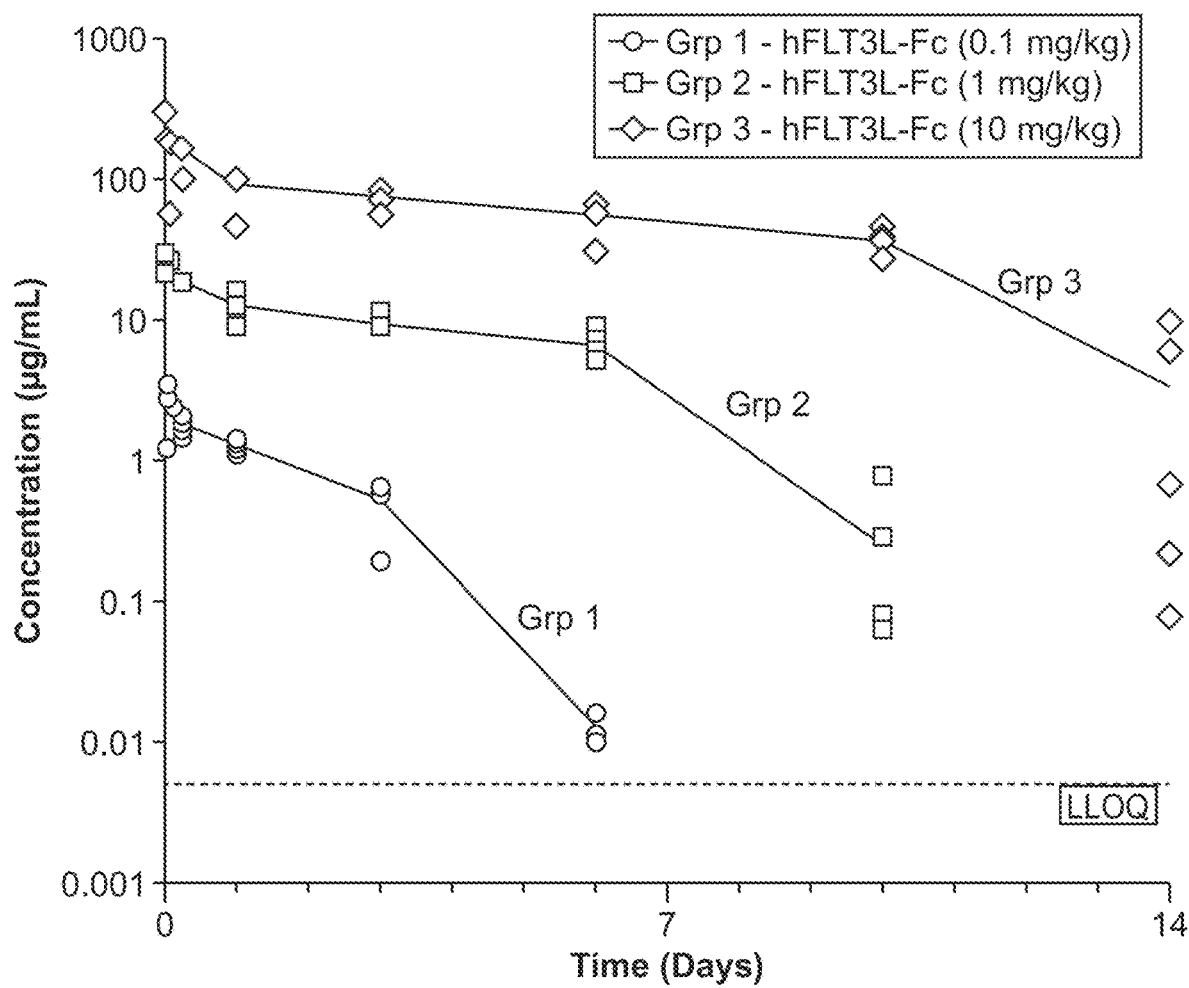
FIG. 5 shows serum concentrations of Flt3L-Fc (SEQ ID NO:28) fusion protein detected in animals dosed with 0.1 mg/kg, 1 mg/kg or 10 mg/kg fusion protein.

The results are graphically presented in FIG. 5.

In Groups 1-3, $C_{max}$ increased nearly dose-proportionally. A more than dose-proportional increase in AUC was observed, suggesting target-mediated drug disposition (TMDD) impacted PK profiles at all dose groups. In addition, total clearance (CL) was observed to be dose-dependent, suggesting target-mediated CL.

Figure 6A:
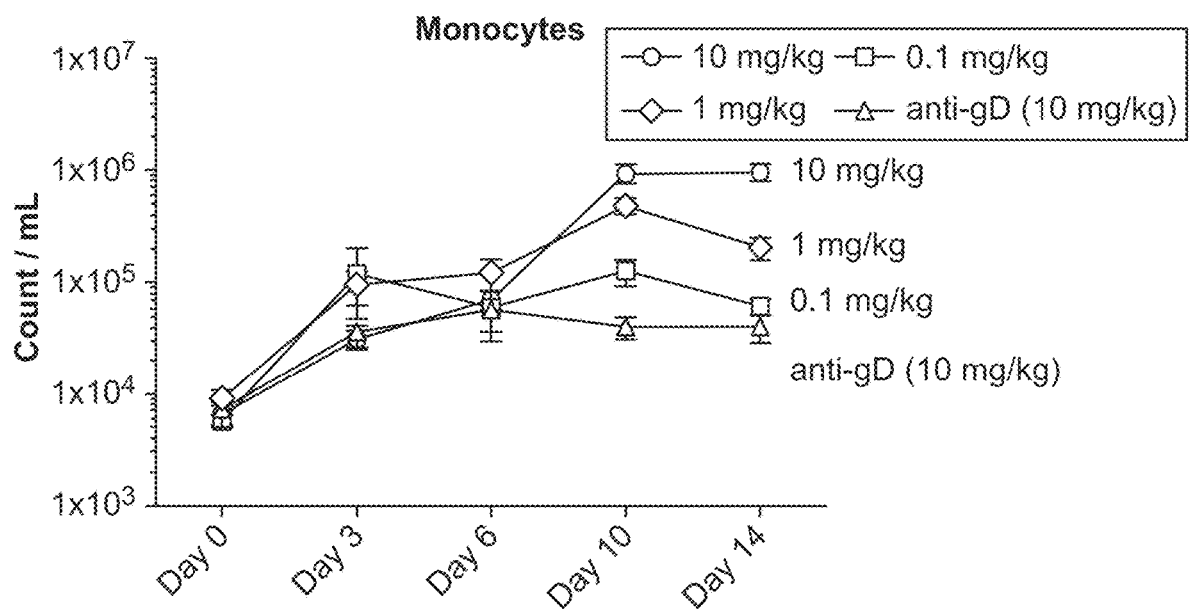
FIGS. 6A-6B show dose-dependent cell expansion of monocytes (FIG. 6A) and DCs (FIG. 6B) in animals administered 0.1 mg/kg, 1 mg/kg or 10 mg/kg fusion protein. Anti-gD is a negative control humanized IgG antibody.
Figure 6B:
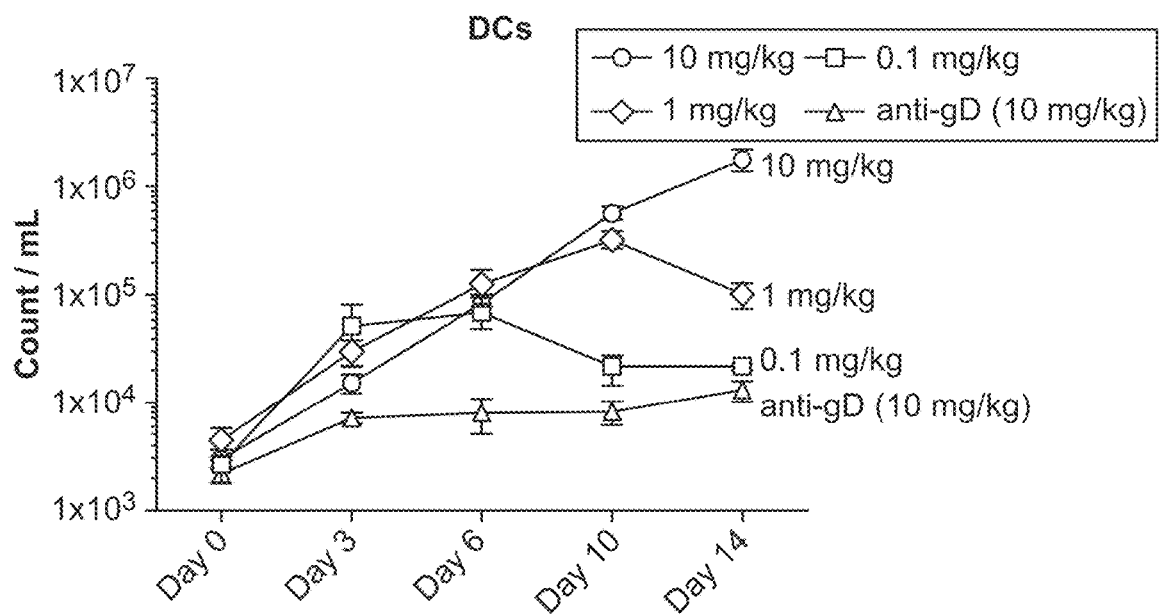

The mean monocyte and DC counts from the peripheral blood samples are shown in FIG. 6A (monocytes) and FIG. 6B (DCs). In all three groups, robust dose-dependent cell expansion was noted in peripheral blood at 0.1-10 mg/kg. The initial kinetics of DC expansion was similar across doses while the duration of expansion was dose/exposure dependent.

Example 6. PKPD Studies in Cynomolgus Monkeys

Additional PKPD studies were performed using varying doses of the Flt3L-Fc (NG2LH) protein (SEQ ID NO:26) administered to cynos. This study was conducted at Charles River Laboratories (Reno, Nev.) using naïve, cynomolgus monkeys. Animals were divided into 4 groups (2 males and 1 female/group). Animals in Group 1 were given Anti-gD (anti-glycoprotein D human IgG1 antibody with N297G mutation) at 10 mg/kg, while animals in Groups 2, 3, and 4 were given FLT3L-Fc at 0.1, 1.0, and 10 mg/kg, respectively. Animals in Group 2 received a single dose whereas animals in other groups were administered two doses (Study Days 1 and 22). Whole blood was collected at selected time points for cell population counts by FACS. Serum was collected and assayed using an anti-huFlt3L-huFc ELISA to determine the amount of test article in each serum sample.

Table 6A below details the dosing of each animal group. Group mean PK parameters are summarized in Table 6B.

TABLE 6A

| Group | Nominal Dose | Treatment |
|---|---|---|
| 1 | 10 mg/kg | Anti-gD (N297G) |
| 2 | 0.1 mg/kg | FLT3L-Fc(NG2LH) |
| 3 | 1 mg/kg | FLT3L-Fc(NG2LH) |
| 4 | 10 mg/kg | FLT3L-Fc(NG2LH) |

TABLE 6B

| Group | Cmax (ug/ml) | Cmax/ Dose (ug/ml)/ (mg/kg) | $AUC_{0-21}$ (ug/ml * day) | $AUC_{0-21}$/Dose (ug/ml * day)/ (mg/kg) | $CL_{0-14}$* (ml/day/ kg) |
|---|---|---|---|---|---|
| 1 | 286 ± 26.6 | 28.6 | 2140 ± 45.9 | 214 | 3.65 |
| 2 | 2.63 ± 0.189 | 26.3 | 6.4 ± 0.285 | 64 | 13.7 |
| 3 | 29.2 ± 0.413 | 29.2 | 141 ± 16.7 | 141 | 6.83 |
| 4 | 280 ± 33.1 | 28 | 1630 ± 386 | 163 | 4.92 |

Figure 7:
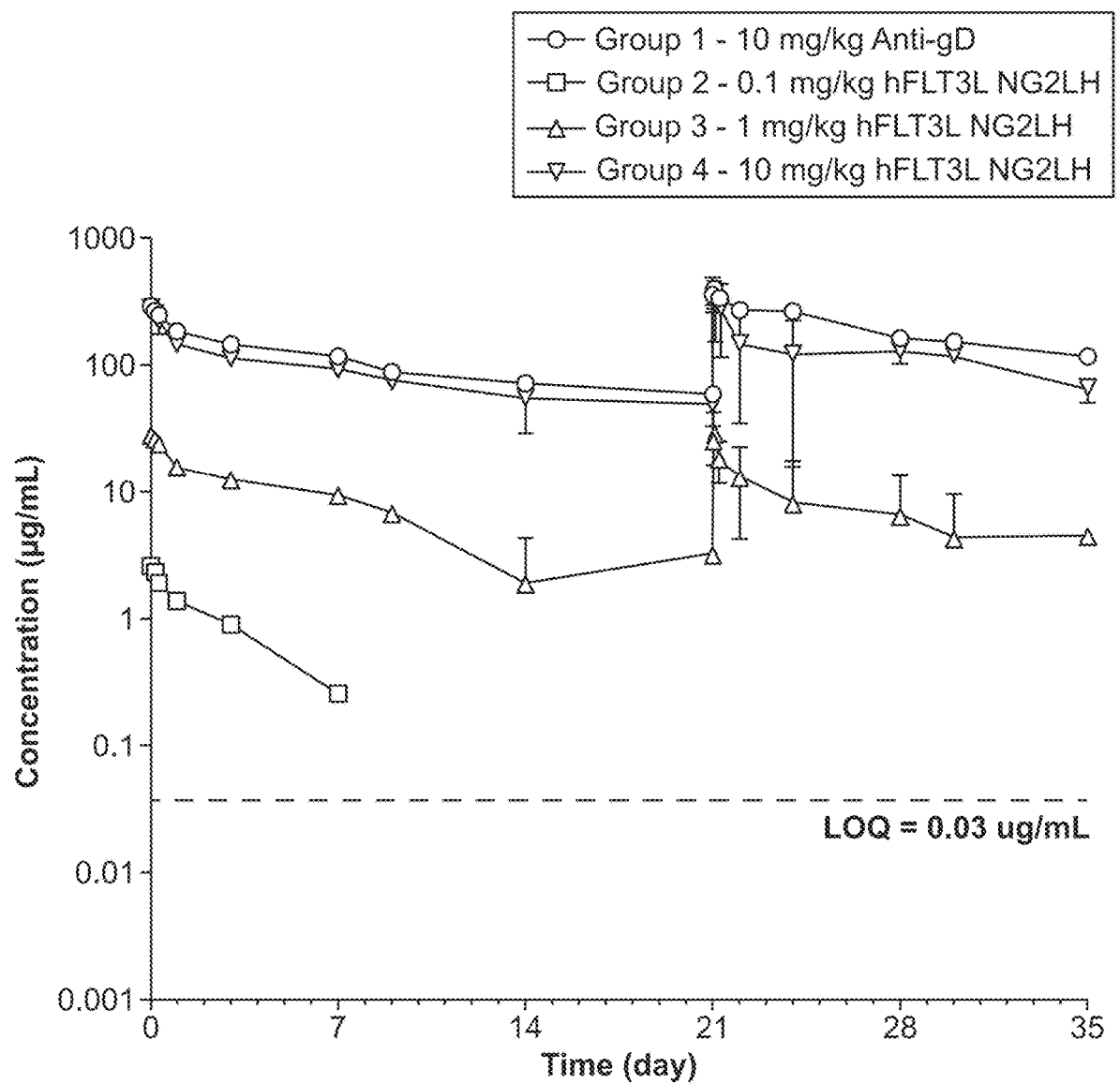
FIG. 7 show plasma concentrations of Flt3L-Fc(NG2LH) in animals administered 0.1 mg/kg, 1 mg/kg or 10 mg/kg fusion protein. Anti-gD is a negative control humanized IgG antibody.

The results are graphically presented in FIG. 7.

In Groups 2-3, $C_{max}$ increase was nearly dose-proportional. Anti-drug-antibody (ADA) was detected in all dosed animals on or after Day 14 and exposures were impacted in animals with high ADA titers. More than dose-proportional increase in $AUC_{0-21}$ was observed after the first dose, suggesting target-mediated drug disposition (TMDD) impacting PK profiles, particularly at ≤1 mg/kg. In addition, total clearance (CL) was observed to be dose-dependent, suggesting target-mediated CL. At 10 mg/kg, the anti-GD and FLT3L-Fc groups had similar PK profiles and the total CL for FLT3L-Fc was 4.92 mL/day/kg.

Figure 8A:
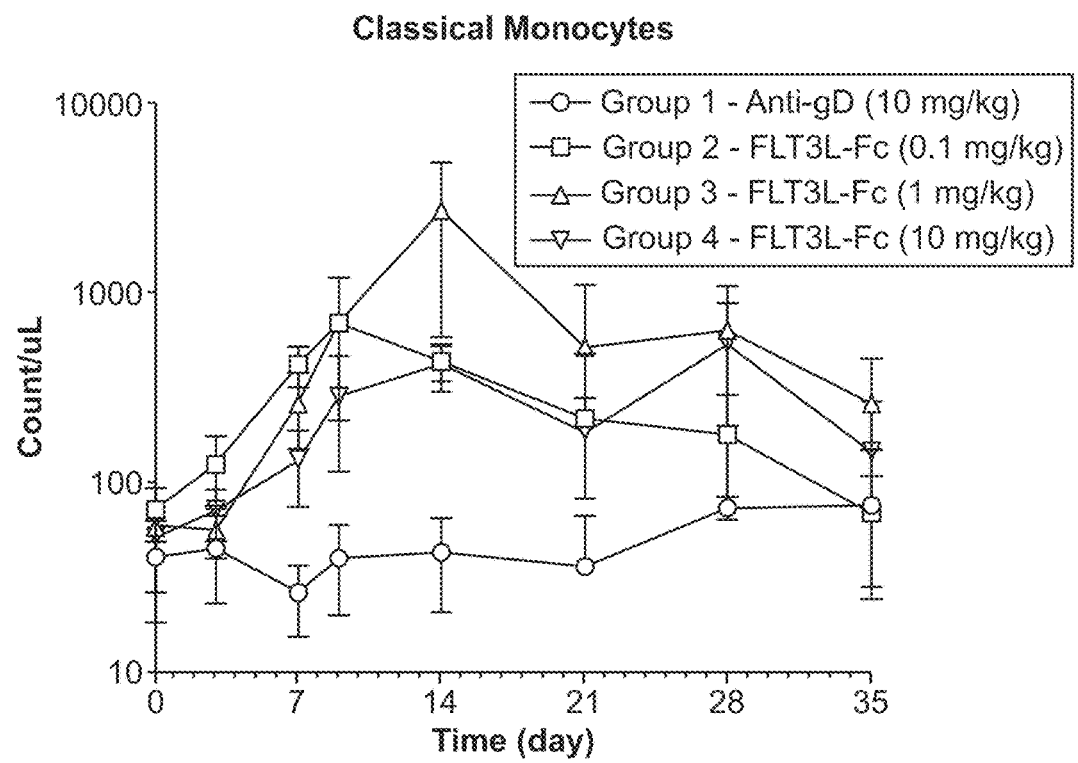
FIGS. 8A-8C show dose-dependent cell expansion of monocytes (FIG. 8A), cDC1 cells (FIG. 8B), and cDC2 cells (FIG. 8C) in animals administered 0.1 mg/kg, 1 mg/kg or 10 mg/kg fusion protein. Anti-IgD is a negative control humanized IgG antibody.
Figure 8B:
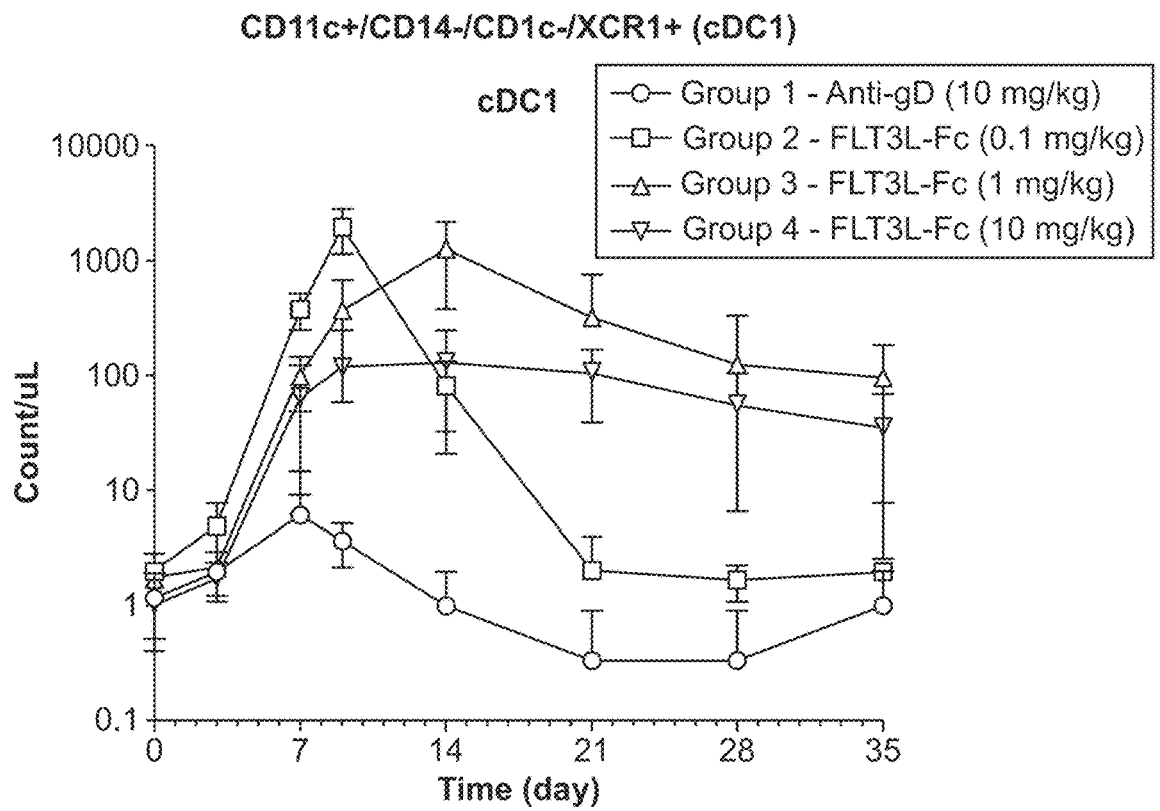
Figure 8C:
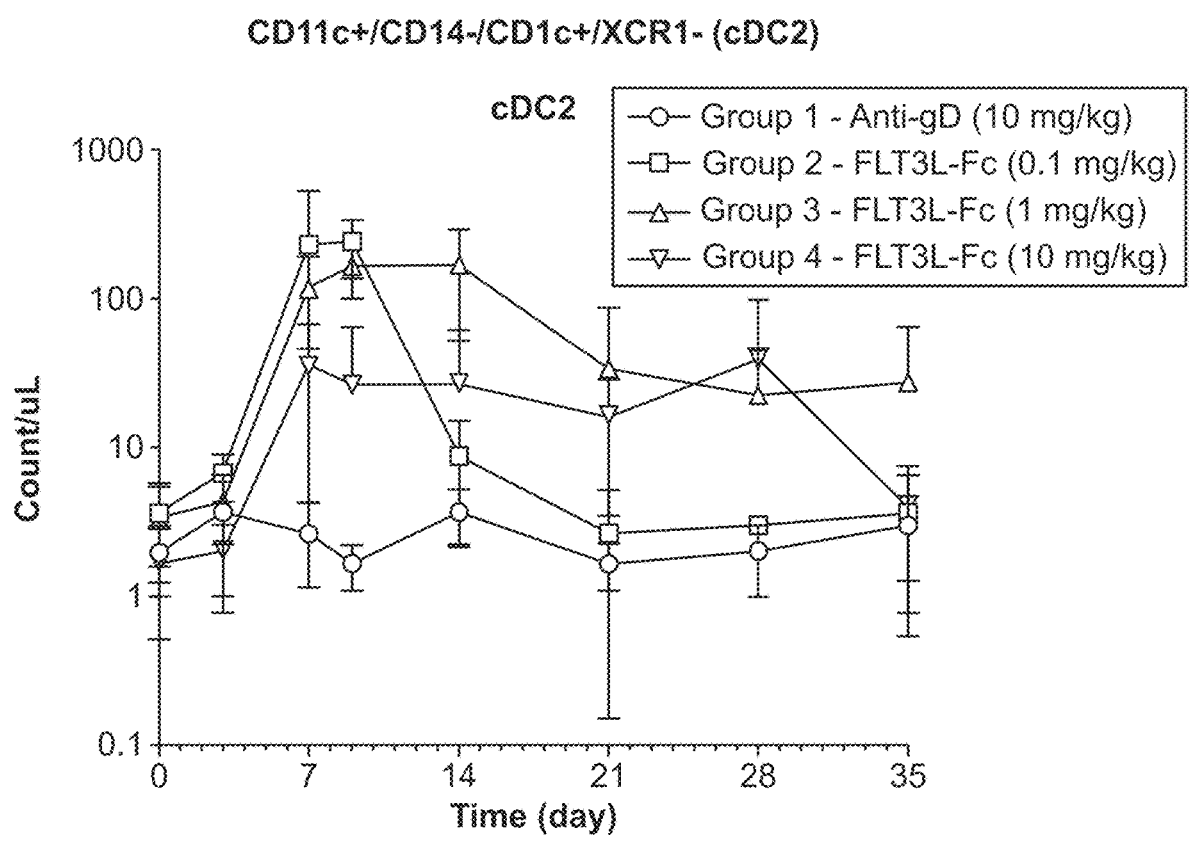

The mean monocyte, cDC1, and cDC2 counts for all four groups is shown in FIGS. 8A-8C. For FLT3L-Fc treated animals, robust dose-dependent cell expansion (monocytes, cDC1, and cDC2) was noted in peripheral blood after 1st dose at 0.1-1 mg/kg. At 10 mg/kg, less expansion was observed. Without being bound by theory, a possible explanation could be that high concentrations of a Flt3 ligand prevent the receptor dimerization required for proliferation and differentiation. At 1-10 mg/kg, lower but sustained cell expansion is observed after the 2nd dose (possibly due to the impact of ADA).

Example 7. FcγR and FcRn Binding of Fc(NG2LH)

Effector function of a Fc domain can be affected by certain amino acid changes within the domain. Accordingly, binding of Fc(NG2LH) to FcγR and FcRn receptors was measured by Biacore. For these assays, FcγRs were captured through anti-His antibody on the Biacore chip or FcRn was directly immobilized on the chip. Data were collected at the end of the injection (association phase) and the relative binding activity (%) was calculated by normalizing the value of the sample divided by the value of the standard.

A summary of the PTD Biocore data is provided in Table 7 below. The values show relative binding level (%) at 10 ug/ml.

TABLE 7

| Antibody | FcγRI αCD20 | FcγRI αHer2 | FcγRI αCD20 | FcγRI αHer2 | FcγRIIIa V158 αCD20 | FcγRIIIa V158 αHer2 | FcRn αCD20 | FcRn αHer2 |
|---|---|---|---|---|---|---|---|---|
| IgG1 wildtype | 100.00 | 100.00 | 100.00 | 100.00 | 100.00 | 100.00 | 100.00 | 100.00 |
| IgG1 LALAPG | 1.74 | 1.92 | −0.34 | −0.62 | 1.36 | 1.58 | 95.93 | 97.86 |
| IgG1 PV A# | 2.69 | 2.51 | 25.11 | 26.77 | 5.16 | 5.57 | 104.45 | 102.81 |
| IgG1 NG | 4.50 | 6.12 | 0.06 | 0.385 | 2.12 | 2.95 | 86.73 | 86.27 |
| IgG1 NG PV A# (NG2LH) | 2.79 | 2.58 | 0.09 | −0.21 | 2.09 | 2.02 | 94.17 | 94.72 |
| IgG1 NG PV A# G | 2.77 | 2.17 | 0.59 | −0.40 | 2.16 | 1.74 | 94.65 | 91.12 |
| IgG1 NG PV A# GSS | 4.00 | 1.99 | 0.81 | −0.47 | 2.24 | 1.46 | 92.92 | 93.24 |
| IgG2 wildtype | 2.43 | 2.10 | 179.04 | 157.56 | 3.85 | 3.33 | 99.42 | 95.35 |
| IgG4 SP | 70.59 | 63.59 | 14.82 | 18.22 | 3.41 | 3.12 | 66.49 | 65.08 |

Example 8. Thermostability of Fc(NG2LH)

Thermostability of the FLT3L ligand fusion protein is one important aspect of developing a therapeutic biologic. After design of the effectorless Fc(NG2LH) protein, differential scanning fluorimetry (DSF) was performed to understand effects of the amino acid changes on thermostability of the Fc protein. DSF monitors thermal unfolding of proteins in the presence of a fluorescent dye and is typically performed by using a real-time PCR instrument (e.g., Bio-Rad CFX). SYPRO orange dye (Invitrogen, cat. no. S6650) is diluted 1:20 in PBS. One ul of diluted dye is added to 24 ul Fab protein (~100 ug/ml) in a well. As the temperature increases from 20° C. to 100° C. in a real-time PCR instrument (Bio-Rad CFX), the fluorescence intensity is plotted and the inflection point of the transition curve (Tm) is calculated using, for example, the Boltzmann equation. See Nature Protocols, 2007, 2:2212-2221.

Variant Fc proteins were analyzed in the context of full-length antibodies, specifically, as an anti-CD20 antibody derived from ocrelizumab and as an anti-Her antibody derived from trastuzumab. The stability data for these variant antibodies are provided in Table 8 below. In addition, variant Fc proteins were also tested in the context of an isolated Fc region comprising the sequences described in Table 2 but absent the CH1 domain and thus beginning N-terminally at the hinge sequence DKTHT. The stability data for these variant Fc proteins are provided in Table 9 below.

TABLE 8

| Construct | Heavy Chain Constant Region SEQ ID NO | a-CD20 IgG (° C.) | a-Her2 IgG (° C.) | Ave. (° C.) | Δ IgG1 (° C.) |
|---|---|---|---|---|---|
| IgG2 wildtype (wt) | 8 | 57 | 57 | 57 | −4.3 |
| IgG4 SP | 9 | 59 | 59 | 59 | −2.3 |
| IgG1 wt | 1 | 61.2 | 61.4 | 61.3 | 0 |
| IgG1 LALAPG | 7 | 59.7 | 59.7 | 59.7 | −1.6 |
| IgG1 PVA# | 4 | 61.9 | 61.95 | 61.9 | +0.6 |
| IgG1 NG | 3 | 52.8 | 53.2 | 53 | −8.3 |
| IgG1 NG PVA# | 2 | 55.2 | 55.6 | 55.4 | −5.9 |
| IgG1 NG PVA# G | 5 | 54.4 | 54.2 | 54.3 | −7.0 |
| IgG1 NG PVA# GSS | 6 | 50.4 | 50 | 50.2 | −11.1 |

TABLE 9

| Construct | SEQ ID NO | Tm (° C.) | Δ IgG1 (° C.) |
|---|---|---|---|
| Fc N297G | 14 | 59.3 | −7.1 |
| Fc NG2LH | 13 | 61.6 | −4.8 |
| Fc PG | 16 | 63.4 | −3.0 |
| Fc LALAPG | 18 | 65.5 | −0.9 |
| Fc wt | 12 | 66.4 | 0.0 |
| LALA | 17 | 67.0 | +0.6 |
| Fc PVA# | 15 | 68.5 | +2.1 |

The data show that for both a full-length IgG and an isolated Fc protein, combining the PVA# variant with the N297G substitution results in an increase in thermostability of about 2° C. relative to the thermostability of the Fc construct having the N297G mutation alone, which was unexpected.

Example 9. Variants of an Effectorless Flt3L-Fc Fusion Protein

Figure 9A:
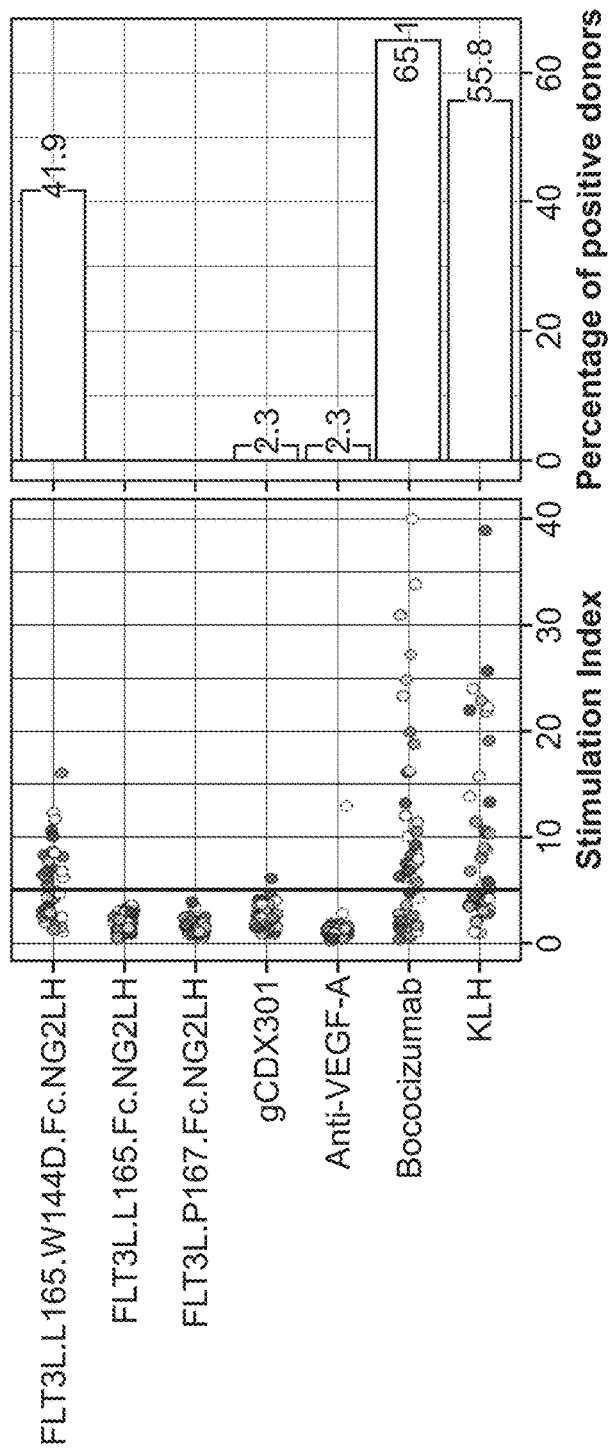
FIG. 9A shows immunogenicity of select Fc-containing proteins.
Figure 9B:
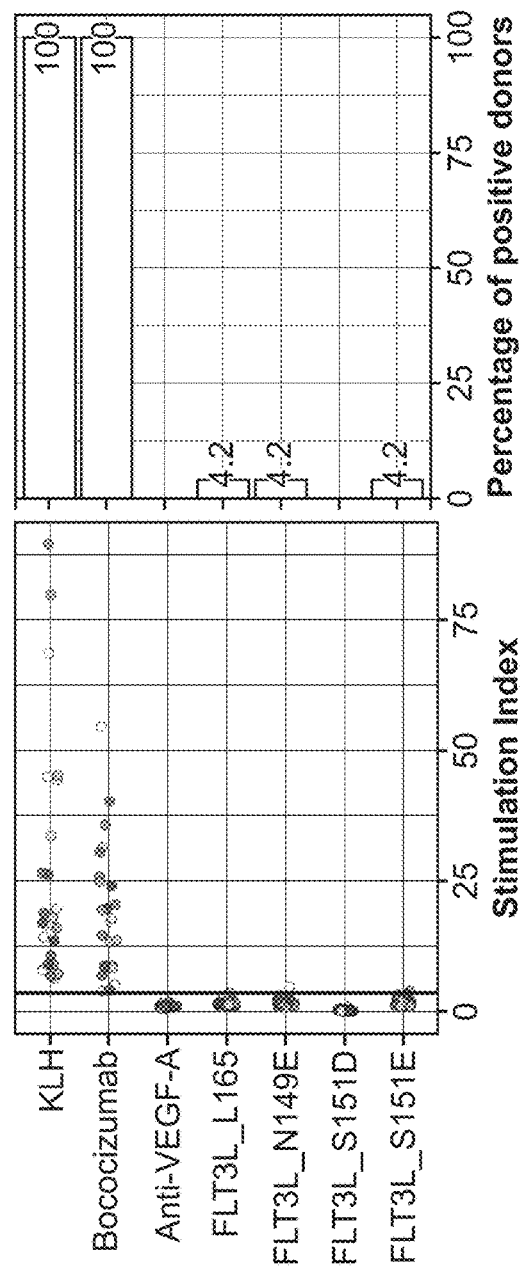
FIG. 9B shows immunogenicity of select Fc-containing proteins.

Experiments were performed to assess immunogenicity of various Flt3L-Fc fusion proteins. Specifically, immunogenicity of certain proteins was tested in a T cell proliferation assay. As shown in FIG. 9A, neither Flt3L.P167.Fc.NG2LH (SEQ ID NO:26) nor Flt3L.L165.Fc.NG2LH (SEQ ID NO:33), had detectable immunogenicity. Unexpectedly, there was significant immunogenicity detected with the introduction of the Flt3L W144D mutation (SEQ ID NO:42).

Another experiment assessed immunogenicity of glycosylation variants of the Flt3L protein. As shown in FIG. 9A, introduction of the N149E, S151D or S151E mutations did not cause any detectable increase in CD4 T cell proliferation. N149E, S151D and S151E indicate the amino acid change and position relative to SEQ ID NO:21.

Example 10. Effectorless Flt3L-Fc Fusion Protein in an ADCP Assay

Experiments were performed to compare the antibody dependent cellular phagocytosis (ADCP) activity of 3 variants of a human recombinant protein Flt3L-Fc construct: 1) Flt3L-Fc-wildtype IgG1 (SEQ ID NO:27) Flt3L with Fc of hIgG1.NG2LH (SEQ ID NO:26) and 3) Flt3L with hIgG1.N297G (SEQ ID NO:28). EB10.hIgG1, an anti-Flt3 monoclonal antibody (Piloto et al., 2006, Cancer Res. 66:4843-4851) was used as a positive control. ADCP assays were carried out using primary monocyte-derived macrophages from healthy human donors as effector cells and SEM, human acute lymphoblastic leukemia cells as target cells. Briefly, primary human macrophages were generated by isolating CD14 positive cells from healthy human PBMCs by positive selection (Miltenyi Biotec Inc, Auburn, Calif.) and cultured in macrophage differentiation media (RPMI 1640, 10% FBS, 1% Glutamax, 1% penicillin/streptomycin, and 20 ng/mL M-CSF (R&D Systems, Minneapolis, Minn.)) at 37° C. in a humidified incubator with 5% $CO_2$. On day 3, cells are stimulated with 50 ng/mL of M-CSF and were cultured for 4 more days. On day 7, macrophages were stained with 10 μM Cell Trace Violet (Thermo Fisher Scientific, Eugene, Oreg.), diluted to $1\times10^6$ cells/mL in ADCP assay media (IMDM, 10% FBS, 1% Glutamax, 1% penicillin/streptomycin), and added at 50 uL/well to a 96 well low adherent U-bottom plate (Costar, Corning, N.Y.). Target SEM cells were diluted in ADCP assay media at $2\times10^6$ cells/mL, pre-labeled with pHrodo (Thermo Fisher Scientific, Eugene, Oreg.), and added (50 uL/well) to the assay plate containing macrophages. Then 100 uL of serial dilutions of test antibodies (table 1) were added to each well containing macrophages and SEM cells, followed by incubation at 37° C. with 5% carbon dioxide for 4.5 hours. The final concentrations of antibodies ranged from 0.457-3000 ng/mL following 3-fold serial dilutions for a total of 11 samples per test antibody. After incubation, the cells were centrifuged at 1200 rpm for 5 min and washed in PBS before being fixed in 4% paraformaldehyde for 10 min at 4° C. The cells were analyzed with a flow cytometer (BD Biosciences FACSCanto IVD 10). Phagocytosis was analyzed via FlowJo (Tree Star, Inc.; Ashland, Oreg.). Cell Trace Violet fluorescence was used to gate the macrophages in the sample population. Phagocytosis was determined by measuring the percentage of pHrodo Green positive macrophages. The degree of phagocytosis was normalized by subtracting the percent pHrodo Green positive macrophages from the control condition (no antibody present). All data points were collected in duplicate. Percent phagocytosis (% ADCP) was plotted opposite antibody concentration and fitted to a four-parameter model using GraphPad Prism (LaJolla, Calif.). This procedure was conducted in independent experiments with 3 donors.

In this study, the Flt3-expressing SEM cells were used as target cells. SEM target cells were pre-labeled with pHrodo AM that fluorescence brightly in acidic pH. As the phagosome containing the target cells becomes increasingly acidic, the pHrodo green fluorescent signal increases, which can be detected on a flow cytometer. ADCP activity induced by Flt3L with Fc of hIgG1.NG2LH (SEQ ID NO:26, 5.1 mg/mL), Flt3L with hIgG1.N297G (SEQ ID NO:28, 1.92 mg/mL), Flt3L with WT IgG1 (SEQ ID NO:27, 2.5 mg/mL) and EB10.hIgG1 (3.17 mg/mL) were examined and compared in three independent experiments using monocyte derived macrophages from three different donors.

Figure 10:
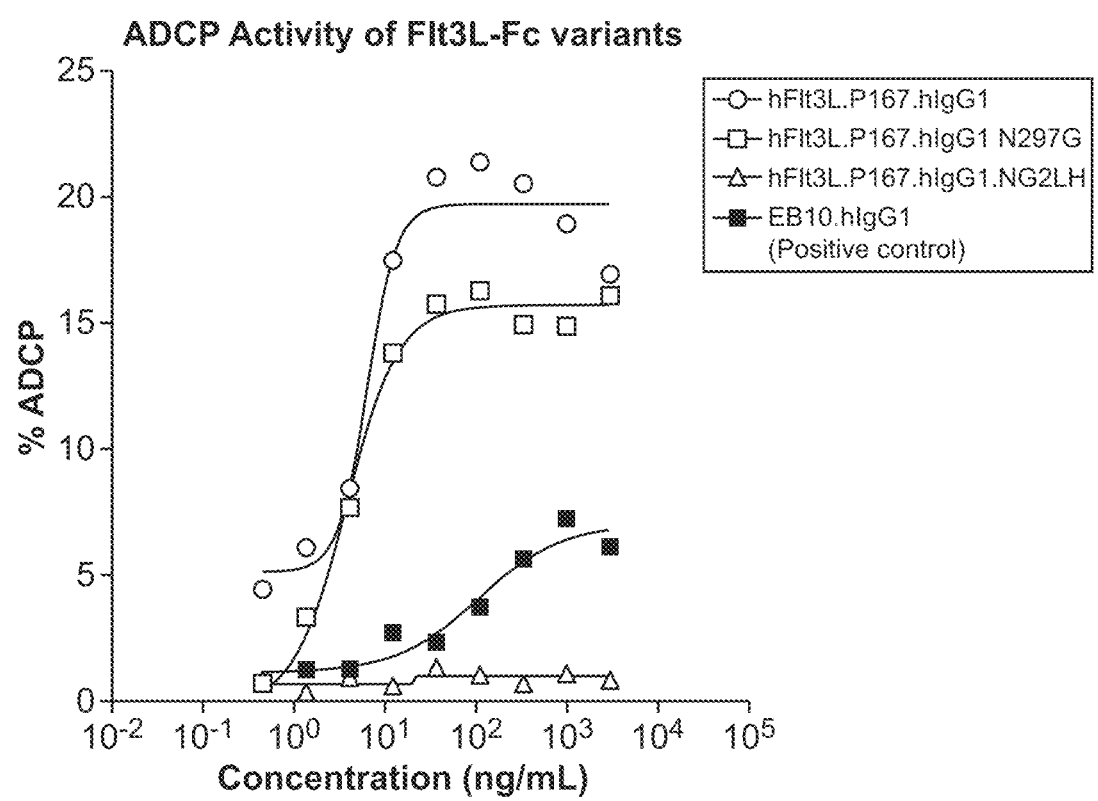
FIG. 10 shows results from one representative in vitro ADCP assay as described in Example 10, comparing ADCP activity of various Flt3L-Fc proteins.

All data points were collected in duplicate, and the mean of the % phagocytosis (% ADCP) was plotted against the concentration of the tested molecule (drug concertation: 3 ug/mL-0.457 ng/mL). The data were fitted with a four-parameter model. A representative dose-response ADCP curve is shown in FIG. 10. Subject to the inherent limitations of the ADCP assay, in all three experiments ADCP activity induced by Flt3L with WT IgG1 and EB10.hIgG1 was observed in Flt3 expressing cells. In addition, FLT3L-Fc-IgG-N297G induced relatively low ADCP while little to no ADCP activity was detected with FLT 3L-Fc-IgG NG2LH.

Additional studies can be done to measure the ADCP activity of additional Flt3L-Fc fusion proteins which comprise the Fc NG2LH (SEQ ID NO:13), such as Flt3L-Fc fusion protein which contain 1, 2, or 3 amino acid substitutions in the Flt3L portion. Such studies can show additional Flt3L-Fc fusion proteins which have little to no ADCP activity, but which can activate expansion of DCs in vivo.

TABLE 10A

| SEQ ID NO: | Description of Heavy Chain Constant Region (CH1 CH3) | Substitution(s) (EU Numbering) | Sequence |
|---|---|---|---|
| 1 | IgG1 WT | | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 2 | IgG1 NG2LH, aka | N297G/E233P/ L234V/L235A/ | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK |

TABLE 10A-continued

SEQUENCE LISTING

| SEQ ID NO: | Description of Heavy Chain Constant Region (CH1 CH3) | Substitution(s) (EU Numbering) | Sequence |
|---|---|---|---|
|  | IgG1 NG PVA# (NG2LH) | G236# | KVEPKSCDKTHTCPPCPAPPVAGPSVFLFPPKPKDTLMISRTPEVTCVVVDVSHEDPEVDGVEVHNAKTKPREEQYGSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 3 | IgG1 NG | N297G | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYGSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 4 | IgG1 PVA# | E233P/L234V/L235A/G236# | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 5 | IgG1 NG PVA#G | N297G/E233P/L234V/L235A/G236#/A327 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKGKVEPKSCDKTHTCPPCPAPPVAGPSVFLFPPKPKDTLMISRTPEVTCVVVDVSHEDPEVDGVEVHNAKTKPREEQYGSTYRVVSVLTVLHQDWLNGKEYKCKVSNKGLPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 6 | IgG1 NG PVA#GSS | N297G/E233P/L234V/L235A/G236#/A327G/A330S/P331S | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVSHEDPEVKFNWYVDGVEVHNAKTKPREEQYGSTYRVVSVLTVLHQDWLNGKEYKCKVSNKGLPSSIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 7 | IgG1 PG | P329G | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 8 | IgG1 LALA | L234A/L235A | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 9 | IgG1 LALAPG | L234A/L235A/P329G | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 10 | IgG2 WT |  | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |

TABLE 10A-continued

SEQUENCE LISTING

| SEQ ID NO: | Description of Heavy Chain Constant Region (CH1 CH3) | Substitution(s) (EU Numbering) | Sequence |
|---|---|---|---|
| 11 | IgG4 SP | S228P | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKR VESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLGK |
| 12 | IgG1 Fc region | | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPSREEMTKNQ VSLTCLVKGFYPSDIAVEWESNGQPENNYKTTPPVLDSDGSFFLYSKL TVDKSRWQQGNVFSCSVMHEALHNHYTQKSLSLSPGK |
| 13 | Fc(NG2LH) | | DKTHTCPPCPAPPVAGPSVFLFPPKPKDTLMISRTPEVTCVVVDVSHED PEVKFNWYVDGVEVHNAKTKPREEQYGSTYRVVSVLTVLHQDWLN GKEYKCKVSNKALPAPIEKTISKAKGQPREPQVYTLPPSREEMTKNQV SLTCLVKGFYPSDIAVEWESNGQPENNYKTTPPVLDSDGSFFLYSKLT VDKSRWQQGNVFSCSVMHEALHNHYTQKSLSLSPGK |

TABLE 10B

SEQUENCE LISTING

| SEQ ID NO: | Construct Name | Sequence |
|---|---|---|
| 14 | IgG1 N297G Fc region | DKTHTCPPCPAPELLGGPSVFLFPPKPKDTLMISRTPEVTC VVVDVSHEDPEVKFNWYVDGVEVHNAKTKPREEQYGST YRVVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK |
| 15 | NVA#Fc region | DKTHTCPPCPAPPVAGPSVFLFPPKPKDTLMISRTPEVTCV VVDVSHEDPEVKFNWYVDGVEVHNAKTKPREEQYNSTY RVVSVLTVLHQDWLNGKEYKCKVSNKALPAPIEKTISKA KGQPREPQVYTLPPSREEMTKNQVSLTCLVKGFYPSDIAV EWESNGQPENNYKTTPPVLDSDGSFFLYSKLTVDKSRWQ QGNVFSCSVMHEALHNHYTQKSLSLSPGK |
| 16 | IgG1 PG Fc domain | DKTHTCPPCPAPELLGGPSVFLFPPKPKDTLMISRTPEVTC VVVDVSHEDPEVKFNWYVDGVEVHNAKTKPREEQYNST YRVVSVLTVLHQDWLNGKEYKCKVSNKALGAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK |
| 17 | IgG1 LALA Fc domain | DKTHTCPPCPAPEAAGGPSVFLFPPKPKDTLMISRTPEVTC VVVDVSHEDPEVKFNWYVDGVEVHNAKTKPREEQYNST YRVVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK |
| 18 | LALAPG Fc region | DKTHTCPPCPAPEAAGGPSVFLFPPKPKDTLMISRTPEVTC VVVDVSHEDPEVKFNWYVDGVEVHNAKTKPREEQYNST YRVVSVLTVLHQDWLNGKEYKCKVSNKALGAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK |
| 19 | LH residues (wt) | ELLG |
| 20 | PVAGP (non-variant part of Fc) | PVAGP |

TABLE 10B-continued

SEQUENCE LISTING

| SEQ ID NO: | Construct Name | Sequence |
|---|---|---|
| 21 | P49771 | MTVLAPAWSPTTYLLLLLLLSSGLSGTQDCSFQHSPISSDF AVKIRELSDYLLQDYPVTVASNLQDEELCGGLWRLVLAQ RWMERLKTVAGSKMQGLLERVNTEIHFVTKCAFQPPPSC LRFVQTNISRLLQETSEQLVALKPWITRQNFSRCLELQCQP DSSTLPPPWSPRPLEATAPTAPQPPLLLLLLLPVGLLLLAA AWCLHWQRTRRRTPRPGEQVPPVPSPQDLLLVEH |
| 22 | Flt3L 27-167 | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPP |
| 23 | CDX-301 | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPPWSPRPLEATAP |
| 24 | Flt3L Signal Sequence | MTVLAPAWSPTTYLLLLLLLSSGLSG |
| 25 | hFLT3L.P168.5aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPPDKTHTCPPCPAPPVAGP SVFLFPPKPKDTLMISRTPEVTCVVVDVSHEDPEVKFNW YVDGVEVHNAKTKPREEQYGSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 26 | hFLT3L.P167.5aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPDKTHTCPPCPAPPVAGPS VFLFPPKPKDTLMISRTPEVTCVVVDVSHEDPEVKFNWY VDGVEVHNAKTKPREEQYGSTYRVVSVLTVLHQDWLNG KEYKCKVSNKALPAPIEKTISKAKGQPREPQVYTLPPSRE EMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 27 | hFLT3L.P167.5aa.hinge.hIgG1 | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPDKTHTCPPCPAPELLGGP SVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 28 | hFLT3L.P167.5aa.hinge.hIgG1.NG | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPDKTHTCPPCPAPELLGGP SVFLFPPKPKDTLMISRTPEVTCVVVDVSHEDPEVKFNW YVDGVEVHNAKTKPREEQYGSTYRVVSVLTVLHQDWLN GKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 29 | hFLT3L.P167.5aa.hinge.hIgG1.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPDKTHTCPPCPAPPVAGPS VFLFPPKPKDTLMISRTPEVTCVVVDVSHEDPEVKFNWY VDGVEVHNAKTKPREEQYNSTYRVVSVLTVLHQDWLNG KEYKCKVSNKALPAPIEKTISKAKGQPREPQVYTLPPSRE EMTKNQVSLTCLVKGFYPSDIAVEWESNGQPENNYKTTP PVLDSDGSFFLYSKLTVDKSRWQQGNVFSCSVMHEALHN HYTQKSLSLSPGK |

TABLE 10B-continued

SEQUENCE LISTING

| SEQ ID NO: | Construct Name | Sequence |
|---|---|---|
| 30 | hFLT3L.P167.5aa.hinge. hIgG1.LALAPG | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVKPW ITRQNFSRCLELQCQPDSSTLPPDKTHTCPPCPAPEAAGGP SVFLFPPKPKDTLMISRTPEVTCVVVDVSHEDPEVKFNW YVDGVEVHNAKTKPREEQYNSTYRVVSVLTVLHQDWLN GKEYKCKVSNKALGAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 31 | hFLT3L.P167.7aa.hinge.hIgG4 | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPESKYGPPCPSCPAPEFLG GPSVFLFPPKPKDTLMISRTPEVTCVVVDVSQEDPEVQFN WYVDGVEVHNAKTKPREEQFNSTYRVVSVLTVLHQDW LNGKEYKCKVSNKGLPSSIEKTISKAKGQPREPQVYTLPP SQEEMTKNQVSLTCLVKGFYPSDIAVEWESNGQPENNYK TTPPVLDSDGSFFLYSRLTVDKSRWQEGNVFSCSVMHEA LHNHYTQKSLSLSLGK |
| 32 | hFLT3L.P166.5aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPDKTHTCPPCPAPPVAGPSV FLFPPKPKDTLMISRTPEVTCVVVDVSHEDPEVKFNWYV DGVEVHNAKTKPREEQYGSTYRVVSVLTVLHQDWLNGK EYKCKVSNKALPAP1EKTISKAKGQPREPQVYTLPPSREE MTKNQVSLTCLVKGFYPSDIAVEWESNGQPENNYKTTPP VLDSDGSFFLYSKLTVDKSRWQQGNVFSCSVMHEALHN HYTQKSLSLSPGK |
| 33 | hFLT3L.L165.5aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLDKTHTCPPCPAPPVAGPSV LFPPKPKDTLMJSRTPEVTCVVVDVSHEDPEVKFNWYVD GVEVHNAKTKPREEQYGSTYRVVSVLTVLHQDWLNGKE YKCKVSNKALPAP1EKTISKAKGQPREPQVYTLPPSREEM TKNQVSLTCLVKGFYPSDIAVEWESNGQPENNYKTTPPV LDSDGSFFLYSKLTVDKSRWQQGNVFSCSVMHEALHNH YTQKSLSLSPGK |
| 34 | hFLT3L.L164.5aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTDKTHTCPPCPAPPVAGPSVFL FPPKPKDTLMISRTPEVTCVVVDVSHEDPEVKFNWYVDG VEVHNAKTKPREEQYGSTYRVVSVLTVLHQDWLNGKEY KCKVSNKALPAP1EKTISKAKGQPREPQVYTLPPSREEMT KNQVSLTCLVKGFYPSDIAVEWESNGQPENNYKTTPPVL DSDGSFFLYSKLTVDKSRWQQGNVFSCSVMHEALHNHY TQKSLSLSPGK |
| 35 | hFLT3L.C158.5aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCDKTHTCPPCPAPPVAGPSVFLFPPKPK DTLMISRTPEVICVVVDVSHEDPEVKFNWYVDGVEVHN AKTKPREEQYGSTYRVVSVLTVLHQDWLNGKEYKCKVS NKALPAPIEKTISKAKGQPREPQVYTLPPSREEMTKNQVS LTCLVKGFYPSDIAVEWESNGQPENNYKTTPPVLDSDGSF FLYSKLTVDKSRWQQGNVFSCSVMHEALHNHYTQKSLS LSPGK |
| 36 | hFLT3L.P179.hIgG1.N297G | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPPWSPRPLEATAPGGGSVT DKTHTCPPCPAPELLGGPSVFLFPPKPKDTLMISRTPEVTC VVVDVSHEDPEVKFNWYVDGVEVHNAKTKPREEQYGST YRVVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW |

TABLE 10B-continued

SEQUENCE LISTING

| SEQ ID NO: | Construct Name | Sequence |
|---|---|---|
| | | QQGNVFSCSVMHEALHNHYTQKSLSLSPGK |
| 37 | hFLT3L.Q159.hIgG1.N297G | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQGGGSVTDKTHTCPPCPAPELLGGPS VFLFPPKPKDTLMISRTPEVTCVVVDVSHEDPEVKFNWY VDGVEVHNAKTKPREEQYGSTYRVVSVLTVLHQDWLNG KEYKCKVSNKALPAPIEKTISKAKGQPREPQVYTLPPSRE EMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 38 | hFTL3L.C158.3aa.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCTHTCPPCPAPPVAGPSVFLFPPKPKDT LMISRTPEVICVVVDVSHEDPEVKFNWYVDGVEVHNAK TKPREEQYGSTYRVVSVLTVLHQDWLNGKEYKCKVSNK ALPAPIEKTISKAKGQPREPQVYTLPPSREEMTKNQVSLT CLVKGFYPSDIAVEWESNGQPENNYKTTPPVLDSDGSFFL YSKLTVDKSRWQQGNVFSCSVMHEALHNHYTQKSLSLS PGK |
| 39 | hFTL3L.C158.no.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCPPCPAPPVAGPSVFLFPPKPKDTLMIS RTPEVTCVVVDVSHEDPEVKFNWYVDGVEVHNAKTKPR EEQYGSTYRVVSVLTVLHQDWLNGKEYKCKVSNKALPA PIEKTISKAKGQPREPQVYTLPPSREEMTKNQVSLTCLVK GFYPSDIAVEWESNGQPENNYKTTPPVLDSDGSFFLYSKL TVDKSRWQQGNVFSCSVMHEALHNHYTQKSLSLSPGK |
| 40 | hFTL3L.D161.no.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDCPPCPAPPVAGPSVFLFPPKPKDT LMISRTPEVICVVVDVSHEDPEVKFNWYVDGVEVHNAK TKPREEQYGSTYRVVSVLTVLHQDWLNGKEYKCKVSNK ALPAPIEKTISKAKGQPREPQVYTLPPSREEMTKNQVSLT CLVKGFYPSDIAVEWESNGQPENNYKTTPPVLDSDGSFFL YSKLTVDKSRWQQGNVFSCSVMHEALHNHYTQKSLSLS PGK |
| 41 | hFTL3L.S163.no.hinge. hIgG1.NG.PVA# | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSCPPCPAPPVAGPSVFLFPPKPK DTLMISRTPEVICVVVDVSHEDPEVKFNWYVDGVEVHN AKTKPREEQYGSTYRVVSVLTVLHQDWLNGKEYKCKVS NKALPAP1EKTISKAKGQPREPQVYTLPPSREEMTKNQVS LTCLVKGFYPSDIAVEWESNGQPENNYKTTPPVLDSDGSF FLYSKLTVDKSRWQQGNVFSCSVMHEALHNHYTQKSLS LSPGK |
| 42 | Hs_FLT3LG.M1-L165.W144D.O.pRK-5aa.hIgG1.NG2LH | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSE-QLVALKPDI TRQNFSRCLELQCQPDSSTLDKTHTCPPCPAPPVAGPSVF LFPPKPKDTLMJSRTPEVTCVVVDVSHEDPEVKFNWYVD GVEVHNAKTKPREEQYGSTYRVVSVLTVLHQDWLNGKE YKCKVSNKALPAP1EKTISKAKGQPREPQVYTLPPSREEM TKNQVSLTCLVKGFYPSDIAVEWESNGQPENNYKTTPPV LDSDGSFFLYSKLTVDKSRWQQGNVFSCSVMHEALHNH YTQKSLSLSPGK |
| 43 | Hs_FLT3LG.M1-L165.S151D.O.pRK-5aa.hIgG1.NG2LH | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFDRCLELQCQPDSSTLDKTHTCPPCPAPPVAGPSVF LFPPKPKDTLMJSRTPEVTCVVVDVSHEDPEVKFNWYVD GVEVHNAKTKPREEQYGSTYRVVSVLTVLHQDWLNGKE |

TABLE 10B-continued

SEQUENCE LISTING

| SEQ ID NO: | Construct Name | Sequence |
|---|---|---|
| | | YKCKVSNKALPAP1EKTISKAKGQPREPQVYTLPPSREEM TKNQVSLTCLVKGFYPSDIAVEWESNGQPENNYKTTPPV LDSDGSFFLYSKLTVDKSRWQQGNVFSCSVMHEALHNH YTQKSLSLSPGK |
| 44 | Hs_FLT3LG.M1-L165.S151E.O.pRK-5aa.hIgG1.NG2LH | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFDRCLELQCQPDSSTLDKTHTCPPCPAPPVAGPSVF LFPPKPKDTLMJSRTPEVTCVVVDVSHEDPEVKFNWYVD GVEVHNAKTKPREEQYGSTYRVVSVLTVLHQDWLNGKE YKCKVSNKALPAPIEKTISKAKGQPREPQVYTLPPSREEM TKNQVSLTCLVKGFYPSDIAVEWESNGQPENNYKTTPPV LDSDGSFFLYSKLTVDKSRWQQGNVFSCSVMHEALHNH YTQKSLSLSPGK |
| 45 | hFLT3L.P167.5aa.hinge.hIgG1.NG.PVA# with native signal sequence | MTVLAPAWSPTTYLLLLLLLSSGLSGTQDCSFQHSPISSDF AVKIRELSDYLLQDYPVTVASNLQDEELCGGLWRLVLAQ RWMERLKTVAGSKMQGLLERVNTEIHFVTKCAFQPPPSC LRFVQTNISRLLQETSEQLVALKPWITRQNFSRCLELQCQP DSSTLPPDKTHTCPPCPAPPVAGPSVFLFPPKPKDTLMISR TPEVTCVVVDVSHEDPEVKFNWYVDGVEVHNAKTKPRE EQYGSTYRVVSVLTVLHQDWLNGKEYKCKVSNKALPAP IEKTISKAKGQPREPQVYTLPPSREEMTKNQVSLTCLVKG FYPSDIAVEWESNGQPENNYKTTPPVLDSDGSFFLYSKLT VDKSRWQQGNVFSCSVMHEALHNHYTQKSLSLSPGK |
| 46 | Flt3L-Fc(IgG4) | TQDCSFQHSPISSDFAVKIRELSDYLLQDYPVTVASNLQD EELCGGLWRLVLAQRWMERLKTVAGSKMQGLLERVNT EIHFVTKCAFQPPPSCLRFVQTNISRLLQETSEQLVALKPW ITRQNFSRCLELQCQPDSSTLPPPWSPRPLEATAPTAPQPP RSPPCPSCPAPEFLGGPSVFLFPPKPKDTLMISRTPEVTCV VVDVSQEDPEVQFNWYVDGVEVHNAKTKPREEQFNSTY RVVSVLTVLHQDWLNGKEYKCKVSNKGLPSSIEKTISKA KGQPREPQVYTLPPSQEEMTKNQVSLTCLVKGFYPSDIA VEWESNGQPENNYKTTPPVLDSDGSFFLYSRLTVDKSRW QEGNVFSCSVMHEALHNHYTQKSLSLSPGK |
| 47 | huMAb4D5-8 | DIQMTQSPSSLSASVGDRVTITCRASQDVNTAVAWYQQK PGKAPKLLIYSASFLYSGVPSRFSGSRSGTDFTLTIS SLQPEDFATYYCQQHYTTPPTFGQGTKVEIK |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A Flt3L-Fc fusion protein comprising the amino acid sequence of SEQ ID NO:26.

2. A Flt3L-Fc fusion protein consisting of the amino acid sequence of SEQ ID NO:26.

3. An isolated nucleic acid encoding the Flt3L-Fc fusion protein of claim 1.

4. A host cell comprising the nucleic acid according to claim 3.

5. The host cell of claim 4, wherein the host cell is a CHO cell or *E. coli*.

6. A method of producing the Flt3L-Fc protein comprising culturing the host cell of claim 4.

7. The method of claim 6, wherein the host cell is a eukaryotic cell or a prokaryotic cell.

8. The method of claim 6, wherein the host cell is a CHO cell.

9. A pharmaceutical formulation comprising a Flt3L-Fc fusion protein comprising SEQ ID NO:26 and a pharmaceutically acceptable carrier.

10. The pharmaceutical formulation of claim 9 further comprising a second therapeutic agent.

11. A method for expanding the number of dendritic cells in a subject, comprising administering to the subject the pharmaceutical composition of claim 10.

12. A method for treating a cancer, comprising administering to a subject in need thereof a pharmaceutical composition comprising a Flt3L-Fc fusion protein comprising SEQ ID NO:26 and a pharmaceutically acceptable carrier.

13. The method of claim 12, further comprising administering to the subject a second therapeutic agent.

14. The method of claim 13, wherein the second therapeutic agent is a dendritic maturation factor.

15. The method of claim 14, wherein the dendritic maturation factor is selected from the group consisting of polyIC, polyICLC, DC40, radiation therapy, and chemotherapy.

16. The method of claim 14, wherein the second therapeutic agent is polyIC.

17. The method of claim 14, wherein the second therapeutic agent is polyICLC.

18. The method of claim 14, wherein the second therapeutic agent is DC40.

19. The method of claim 14, wherein the second therapeutic agent is radiation therapy.

20. The method of claim 14, wherein the second therapeutic agent is chemotherapy.

21. The method of claim 13, wherein the second therapeutic agent is a checkpoint inhibitor.

22. The method of claim 21, wherein the checkpoint inhibitor is an antibody which specifically binds to PD-L1.

23. The method of claim 21, wherein the checkpoint inhibitor is an antibody which specifically binds to PD-1.

24. The method of claim 23, wherein the checkpoint inhibitor is an antibody which specifically binds to CTLA-4.

25. The method of claim 12, further comprising administering to the subject:
a second therapeutic agent which is a dendritic maturation factor, and
a third therapeutic agent which is a checkpoint inhibitor.

26. The method of claim 15, wherein the dendritic maturation factor is polyIC, polyICLC, DC40, radiation therapy, and/or chemotherapy, and the checkpoint inhibitor is an antibody which specifically binds to PD-L1, PD-1, and/or CTLA-4.

* * * * *

```
                        SEQUENCE LISTING

<160> NUMBER OF SEQ ID NOS: 53

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Gly Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 3
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 5
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125
```

```
Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Gly Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 6
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140
```

```
Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Gly Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 7
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 8
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Ala Ala Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

```
His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 11
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 227
<212> TYPE: PRT
<213> ORGANISM: Homo sapiens

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 226
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 13

Asp Lys Thr His Thr Cys Pro Pro Cys Pro Ala Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Gly Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 14
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gly Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190
```

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
210                 215                 220

Gly Lys
225

<210> SEQ ID NO 16
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 17
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 18
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 19
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Glu Leu Leu Gly
1

<210> SEQ ID NO 20
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Pro Val Ala Gly Pro
1               5

<210> SEQ ID NO 21
<211> LENGTH: 235
<212> TYPE: PRT
<213> ORGANISM: Homo sapiens

<400> SEQUENCE: 21

Met Thr Val Leu Ala Pro Ala Trp Ser Pro Thr Thr Tyr Leu Leu Leu
1               5                   10                  15
Leu Leu Leu Leu Ser Ser Gly Leu Ser Gly Thr Gln Asp Cys Ser Phe
                20                  25                  30
Gln His Ser Pro Ile Ser Ser Asp Phe Ala Val Lys Ile Arg Glu Leu
            35                  40                  45
Ser Asp Tyr Leu Leu Gln Asp Tyr Pro Val Thr Val Ala Ser Asn Leu
    50                  55                  60
```

```
Gln Asp Glu Leu Cys Gly Gly Leu Trp Arg Leu Val Leu Ala Gln
 65                  70                  75                  80

Arg Trp Met Glu Arg Leu Lys Thr Val Ala Gly Ser Lys Met Gln Gly
                 85                  90                  95

Leu Leu Glu Arg Val Asn Thr Glu Ile His Phe Val Thr Lys Cys Ala
            100                 105                 110

Phe Gln Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
        130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Trp Ser Pro Arg Pro Leu Glu Ala
                165                 170                 175

Thr Ala Pro Thr Ala Pro Gln Pro Pro Leu Leu Leu Leu Leu Leu
                180                 185                 190

Pro Val Gly Leu Leu Leu Ala Ala Ala Trp Cys Leu His Trp Gln
            195                 200                 205

Arg Thr Arg Arg Thr Pro Arg Pro Gly Glu Gln Val Pro Pro Val
210                 215                 220

Pro Ser Pro Gln Asp Leu Leu Val Glu His
225                 230                 235

<210> SEQ ID NO 22
<211> LENGTH: 141
<212> TYPE: PRT
<213> ORGANISM: Homo sapiens

<400> SEQUENCE: 22

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
         50                 55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro
        130                 135                 140

<210> SEQ ID NO 23
<211> LENGTH: 153
<212> TYPE: PRT
<213> ORGANISM: Homo sapiens

<400> SEQUENCE: 23

Thr Gln Asp Cys Ser Phe Gln His Ser Pro Ile Ser Ser Asp Phe Ala
 1               5                  10                  15
```

-continued

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
            130                 135                 140

Pro Arg Pro Leu Glu Ala Thr Ala Pro
145                 150

<210> SEQ ID NO 24
<211> LENGTH: 26
<212> TYPE: PRT
<213> ORGANISM: Homo sapiens

<400> SEQUENCE: 24

Met Thr Val Leu Ala Pro Ala Trp Ser Pro Thr Thr Tyr Leu Leu Leu
1               5                   10                  15

Leu Leu Leu Leu Ser Ser Gly Leu Ser Gly
            20                  25

<210> SEQ ID NO 25
<211> LENGTH: 368
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 25

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

-continued

```
Glu Leu Gln Cys Gln Pro Asp Ser Ser Thr Leu Pro Pro Asp Lys
    130                 135                 140

Thr His Thr Cys Pro Pro Cys Pro Ala Pro Pro Val Ala Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Gly Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 26
<211> LENGTH: 367
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110
```

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Asp Lys Thr
        130                 135                 140

His Thr Cys Pro Pro Cys Pro Ala Pro Pro Val Ala Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Gly Ser Thr Tyr Arg Val Val Ser
210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Glu Glu Met Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 27
<211> LENGTH: 368
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

```
Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Asp Lys Thr
130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 28
<211> LENGTH: 368
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80
```

```
Phe Val Thr Lys Cys Ala Phe Gln Pro Pro Ser Cys Leu Arg Phe
             85                  90                  95

Val Gln Thr Asn Ile Ser Arg Leu Leu Gln Glu Thr Ser Glu Gln Leu
        100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Asp Lys Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Gly Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 29
<211> LENGTH: 367
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60
```

```
Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Asp Lys Thr
130                 135                 140

His Thr Cys Pro Pro Cys Pro Ala Pro Pro Val Ala Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Glu Glu Met Thr Lys Asn Gln Val Ser Leu Thr Cys Leu
        275                 280                 285

Val Lys Gly Phe Tyr Pro Ser Asp Ile Ala Val Glu Trp Glu Ser Asn
290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 30
<211> LENGTH: 368
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45
```

```
Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Asp Lys Thr
130                 135                 140

His Thr Cys Pro Pro Cys Pro Ala Pro Glu Ala Ala Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Gly Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 31
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Leu Gln Asp Tyr Pro Val
            20                  25                  30
```

```
Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Glu Ser Lys
            130                 135                 140

Tyr Gly Pro Pro Cys Pro Ser Cys Pro Ala Pro Glu Phe Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Asp Val Ser Gln Glu
                180                 185                 190

Asp Pro Glu Val Gln Phe Asn Trp Tyr Val Asp Gly Val Glu Val His
                195                 200                 205

Asn Ala Lys Thr Lys Pro Arg Glu Glu Gln Phe Asn Ser Thr Tyr Arg
            210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
                260                 265                 270

Thr Leu Pro Pro Ser Gln Glu Glu Met Thr Lys Asn Gln Val Ser Leu
            275                 280                 285

Thr Cys Leu Val Lys Gly Phe Tyr Pro Ser Asp Ile Ala Val Glu Trp
            290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Met His
                340                 345                 350

Glu Ala Leu His Asn His Tyr Thr Gln Lys Ser Leu Ser Leu Ser Leu
            355                 360                 365

Gly Lys
    370

<210> SEQ ID NO 32
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 32

```
Thr Gln Asp Cys Ser Phe Gln His Ser Pro Ile Ser Ser Asp Phe Ala
1               5                   10                  15
Val Lys Ile Arg Glu Leu Ser Asp Tyr Leu Leu Gln Asp Tyr Pro Val
            20                  25                  30
Thr Val Ala Ser Asn Leu Gln Asp Glu Glu Leu Cys Gly Gly Leu Trp
        35                  40                  45
Arg Leu Val Leu Ala Gln Arg Trp Met Glu Arg Leu Lys Thr Val Ala
    50                  55                  60
Gly Ser Lys Met Gln Gly Leu Leu Glu Arg Val Asn Thr Glu Ile His
65                  70                  75                  80
Phe Val Thr Lys Cys Ala Phe Gln Pro Pro Ser Cys Leu Arg Phe
                85                  90                  95
Val Gln Thr Asn Ile Ser Arg Leu Leu Gln Glu Thr Ser Glu Gln Leu
                100                 105                 110
Val Ala Leu Lys Pro Trp Ile Thr Arg Gln Asn Phe Ser Arg Cys Leu
            115                 120                 125
Glu Leu Gln Cys Gln Pro Asp Ser Ser Thr Leu Pro Asp Lys Thr His
130                 135                 140
Thr Cys Pro Pro Cys Pro Ala Pro Pro Val Ala Gly Pro Ser Val Phe
145                 150                 155                 160
Leu Phe Pro Pro Lys Pro Lys Asp Thr Leu Met Ile Ser Arg Thr Pro
                165                 170                 175
Glu Val Thr Cys Val Val Val Asp Val Ser His Glu Asp Pro Glu Val
            180                 185                 190
Lys Phe Asn Trp Tyr Val Asp Gly Val Glu Val His Asn Ala Lys Thr
        195                 200                 205
Lys Pro Arg Glu Glu Gln Tyr Gly Ser Thr Tyr Arg Val Val Ser Val
    210                 215                 220
Leu Thr Val Leu His Gln Asp Trp Leu Asn Gly Lys Glu Tyr Lys Cys
225                 230                 235                 240
Lys Val Ser Asn Lys Ala Leu Pro Ala Pro Ile Glu Lys Thr Ile Ser
                245                 250                 255
Lys Ala Lys Gly Gln Pro Arg Glu Pro Gln Val Tyr Thr Leu Pro Pro
            260                 265                 270
Ser Arg Glu Glu Met Thr Lys Asn Gln Val Ser Leu Thr Cys Leu Val
        275                 280                 285
Lys Gly Phe Tyr Pro Ser Asp Ile Ala Val Glu Trp Glu Ser Asn Gly
    290                 295                 300
Gln Pro Glu Asn Asn Tyr Lys Thr Thr Pro Pro Val Leu Asp Ser Asp
305                 310                 315                 320
Gly Ser Phe Phe Leu Tyr Ser Lys Leu Thr Val Asp Lys Ser Arg Trp
                325                 330                 335
Gln Gln Gly Asn Val Phe Ser Cys Ser Val Met His Glu Ala Leu His
            340                 345                 350
Asn His Tyr Thr Gln Lys Ser Leu Ser Leu Ser Pro Gly Lys
        355                 360                 365
```

<210> SEQ ID NO 33
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 33

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Asp Lys Thr His Thr
    130                 135                 140

Cys Pro Pro Cys Pro Ala Pro Pro Val Ala Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Gly Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Glu Glu Met Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365
```

<210> SEQ ID NO 34
<211> LENGTH: 364
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Asp Lys Thr His Thr Cys
    130                 135                 140

Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Gly Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 35
<211> LENGTH: 358

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Asp Lys Thr His Thr Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Gly
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355
```

```
<210> SEQ ID NO 36
<211> LENGTH: 386
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Pro Gly Gly Gly Ser Val Thr Asp
145                 150                 155                 160

Lys Thr His Thr Cys Pro Pro Cys Pro Ala Pro Glu Leu Leu Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser His Glu
        195                 200                 205

Asp Pro Glu Val Lys Phe Asn Trp Tyr Val Asp Gly Val Glu Val His
210                 215                 220

Asn Ala Lys Thr Lys Pro Arg Glu Glu Gln Tyr Gly Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Arg Glu Glu Met Thr Lys Asn Gln Val Ser Leu
290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365
```

```
Glu Ala Leu His Asn His Tyr Thr Gln Lys Ser Leu Ser Leu Ser Pro
    370                 375                 380

Gly Lys
385

<210> SEQ ID NO 37
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Gly Gly Gly Ser Val Thr Asp Lys Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Gly Ser Thr Tyr Arg Val Val Ser Val
210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
290                 295                 300

Gln Pro Glu Asn Asn Tyr Lys Thr Thr Pro Pro Val Leu Asp Ser Asp
305                 310                 315                 320
```

```
Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 38
<211> LENGTH: 356
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Thr His Thr Cys Pro Pro Cys Pro Ala Pro Pro Val
    130                 135                 140

Ala Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Gly Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300
```

```
Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
            325                 330                 335

Met His Glu Ala Leu His Asn His Tyr Thr Gln Lys Ser Leu Ser Leu
        340                 345                 350

Ser Pro Gly Lys
        355

<210> SEQ ID NO 39
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Gly Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285
```

```
Asn Gly Gln Pro Glu Asn Asn Tyr Lys Thr Thr Pro Pro Val Leu Asp
        290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 40
<211> LENGTH: 356
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Cys Pro Pro Cys Ala Pro Pro Pro Val
    130                 135                 140

Ala Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Gly Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285
```

```
Glu Trp Glu Ser Asn Gly Gln Pro Glu Asn Asn Tyr Lys Thr Thr Pro
        290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 41
<211> LENGTH: 358
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Cys Pro Pro Cys Pro Ala Pro
130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Gly
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270
```

```
Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
        290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 42
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Asp Ile Thr Arg Gln Asn Phe Ser Arg Cys Leu
        115                 120                 125

Glu Leu Gln Cys Gln Pro Asp Ser Ser Thr Leu Asp Lys Thr His Thr
    130                 135                 140

Cys Pro Pro Cys Pro Ala Pro Pro Val Ala Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Gly Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255
```

```
Ala Lys Gly Gln Pro Arg Glu Pro Gln Val Tyr Thr Leu Pro Pro Ser
                260                 265                 270

Arg Glu Glu Met Thr Lys Asn Gln Val Ser Leu Thr Cys Leu Val Lys
            275                 280                 285

Gly Phe Tyr Pro Ser Asp Ile Ala Val Glu Trp Glu Ser Asn Gly Gln
        290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365

<210> SEQ ID NO 43
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Asp Arg Cys Leu
        115                 120                 125

Glu Leu Gln Cys Gln Pro Asp Ser Ser Thr Leu Asp Lys Thr His Thr
    130                 135                 140

Cys Pro Pro Cys Pro Ala Pro Pro Val Ala Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Gly Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240
```

```
Val Ser Asn Lys Ala Leu Pro Ala Pro Ile Glu Lys Thr Ile Ser Lys
            245                 250                 255

Ala Lys Gly Gln Pro Arg Glu Pro Gln Val Tyr Thr Leu Pro Pro Ser
        260                 265                 270

Arg Glu Glu Met Thr Lys Asn Gln Val Ser Leu Thr Cys Leu Val Lys
    275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
                355                 360                 365

<210> SEQ ID NO 44
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Asp Arg Cys Leu
        115                 120                 125

Glu Leu Gln Cys Gln Pro Asp Ser Ser Thr Leu Asp Lys Thr His Thr
130                 135                 140

Cys Pro Pro Cys Pro Ala Pro Pro Val Ala Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Gly Ser Thr Tyr Arg Val Val Ser Val Leu
    210                 215                 220
```

-continued

```
Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
            245                 250                 255

Ala Lys Gly Gln Pro Arg Glu Pro Gln Val Tyr Thr Leu Pro Pro Ser
        260                 265                 270

Arg Glu Glu Met Thr Lys Asn Gln Val Ser Leu Thr Cys Leu Val Lys
    275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
            325                 330                 335

Gln Gly Asn Val Phe Ser Cys Ser Val Met His Glu Ala Leu His Asn
        340                 345                 350

His Tyr Thr Gln Lys Ser Leu Ser Leu Ser Pro Gly Lys
    355                 360                 365
```

```
<210> SEQ ID NO 45
<211> LENGTH: 393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Asp Lys Thr His Thr Cys Pro Pro Cys
                165                 170                 175

Pro Ala Pro Pro Val Ala Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205
```

```
Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Gly Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
                260                 265                 270

Ala Leu Pro Ala Pro Ile Glu Thr Ile Ser Lys Ala Lys Gly Gln
                275                 280                 285

Pro Arg Glu Pro Gln Val Tyr Thr Leu Pro Pro Ser Arg Glu Glu Met
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
                340                 345                 350

Tyr Ser Lys Leu Thr Val Asp Lys Ser Arg Trp Gln Gln Gly Asn Val
                355                 360                 365

Phe Ser Cys Ser Val Met His Glu Ala Leu His Asn His Tyr Thr Gln
                370                 375                 380

Lys Ser Leu Ser Leu Ser Pro Gly Lys
385                 390

<210> SEQ ID NO 46
<211> LENGTH: 385
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Arg
145                 150                 155                 160
```

```
Ser Pro Pro Cys Pro Ser Cys Pro Ala Pro Glu Phe Leu Gly Gly Pro
                165                 170                 175
Ser Val Phe Leu Phe Pro Pro Lys Pro Lys Asp Thr Leu Met Ile Ser
            180                 185                 190
Arg Thr Pro Glu Val Thr Cys Val Val Val Asp Val Ser Gln Glu Asp
        195                 200                 205
Pro Glu Val Gln Phe Asn Trp Tyr Val Asp Gly Val Glu Val His Asn
    210                 215                 220
Ala Lys Thr Lys Pro Arg Glu Glu Gln Phe Asn Ser Thr Tyr Arg Val
225                 230                 235                 240
Val Ser Val Leu Thr Val Leu His Gln Asp Trp Leu Asn Gly Lys Glu
                245                 250                 255
Tyr Lys Cys Lys Val Ser Asn Lys Gly Leu Pro Ser Ser Ile Glu Lys
            260                 265                 270
Thr Ile Ser Lys Ala Lys Gly Gln Pro Arg Glu Pro Gln Val Tyr Thr
        275                 280                 285
Leu Pro Pro Ser Gln Glu Glu Met Thr Lys Asn Gln Val Ser Leu Thr
    290                 295                 300
Cys Leu Val Lys Gly Phe Tyr Pro Ser Asp Ile Ala Val Glu Trp Glu
305                 310                 315                 320
Ser Asn Gly Gln Pro Glu Asn Asn Tyr Lys Thr Thr Pro Pro Val Leu
                325                 330                 335
Asp Ser Asp Gly Ser Phe Phe Leu Tyr Ser Arg Leu Thr Val Asp Lys
            340                 345                 350
Ser Arg Trp Gln Glu Gly Asn Val Phe Ser Cys Ser Val Met His Glu
        355                 360                 365
Ala Leu His Asn His Tyr Thr Gln Lys Ser Leu Ser Leu Ser Pro Gly
    370                 375                 380
Lys
385

<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys
            100                 105
```

<210> SEQ ID NO 48
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Pro Trp Ser Pro Arg Pro Leu Glu Ala Thr Ala Pro Thr Ala Pro Gln
1               5                   10                  15

Pro Pro

<210> SEQ ID NO 49
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Trp Ser Pro Arg Pro Leu Glu Ala Thr Ala Pro Thr Ala Pro Gln Pro
1               5                   10                  15

Pro

<210> SEQ ID NO 50
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ser Pro Arg Pro Leu Glu Ala Thr Ala Pro Thr Ala Pro Gln Pro Pro
1               5                   10                  15

<210> SEQ ID NO 51
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Pro Arg Pro Leu Glu Ala Thr Ala Pro Thr Ala Pro Gln Pro Pro
1               5                   10                  15

<210> SEQ ID NO 52
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Arg Pro Leu Glu Ala Thr Ala Pro Thr Ala Pro Gln Pro Pro
1               5                   10

```
<210> SEQ ID NO 53
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Pro Leu Glu Ala Thr Ala Pro Thr Ala Pro Gln Pro Pro
1               5                   10
```